(12) United States Patent
Lambers et al.

(10) Patent No.: US 11,957,418 B2
(45) Date of Patent: *Apr. 16, 2024

(54) SYSTEMS AND METHODS FOR PRE-OPERATIVE VISUALIZATION OF A JOINT

(71) Applicant: Stryker Corporation, Kalamazoo, MI (US)

(72) Inventors: Floor Lambers, Basel (CH); William Kaiser, Campbell, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,449

(22) Filed: Oct. 10, 2022

(65) Prior Publication Data
US 2023/0210599 A1 Jul. 6, 2023

Related U.S. Application Data

(63) Continuation of application No. 16/261,464, filed on Jan. 29, 2019, now Pat. No. 11,464,569.
(Continued)

(51) Int. Cl.
*A61B 5/00* (2006.01)
*A61B 5/06* (2006.01)
(Continued)

(52) U.S. Cl.
CPC .......... *A61B 34/10* (2016.02); *A61F 2/30942* (2013.01); *G06F 30/00* (2020.01);
(Continued)

(58) Field of Classification Search
CPC .............. A61B 34/10; A61B 2017/564; A61B 2034/102; A61F 2/30942; G06F 30/00
See application file for complete search history.

(56) References Cited

U.S. PATENT DOCUMENTS 5,862,249 A 1/1999 Jang et al.
6,161,080 A 12/2000 Aouni-Ateshian et al.
(Continued)

FOREIGN PATENT DOCUMENTS

CN 101518447 A 9/2009
CN 102194047 A 9/2011
(Continued)

OTHER PUBLICATIONS

Agus et al. (2003). "A haptic model of a bone-cutting burr," Studies in Health Technology and Informatics 94: 4-10.
(Continued)

*Primary Examiner* — Maroun P Kanaan
(74) *Attorney, Agent, or Firm* — Morrison & Foerster LLP

(57) ABSTRACT

A method for displaying graphical indications associated with a joint includes: receiving image data associated with a joint of a subject; generating a three-dimensional model of at least a portion of the joint of the subject using the image data; identifying at least one region of the joint that deviates from a baseline anatomy by comparing at least a portion of the three-dimensional model to a baseline model; generating at least one measurement of a characteristic of the joint at one or more predefined locations using the three-dimensional model and a coordinate system; displaying a spectrum bar graph that comprises at least one representation of the at least one measurement of the characteristic of the joint; determining a pathology associated with the joint based on the at least one measurement of the characteristic of the joint; and displaying at least one graphical indication indicating the pathology associated with the joint.

21 Claims, 20 Drawing Sheets

Related U.S. Application Data

(60) Provisional application No. 62/623,068, filed on Jan. 29, 2018.

(51) Int. Cl.
| | | |
|---|---|---|
| *A61B 34/10* | (2016.01) | |
| *A61B 34/20* | (2016.01) | |
| *A61F 2/30* | (2006.01) | |
| *G06F 30/00* | (2020.01) | |
| *A61B 17/56* | (2006.01) | |

(52) U.S. Cl.
CPC ... *A61B 2017/564* (2013.01); *A61B 2034/102* (2016.02); *A61B 2034/105* (2016.02)

(56) References Cited

U.S. PATENT DOCUMENTS

| | | | |
|---|---|---|---|
| 6,205,411 | B1 | 3/2001 | Digioia, III et al. |
| 6,697,664 | B2 | 2/2004 | Kienzle, III et al. |
| 7,167,738 | B2 | 1/2007 | Schweikard et al. |
| 7,231,076 | B2 | 6/2007 | Fu et al. |
| 7,327,865 | B2 | 2/2008 | Fu et al. |
| 7,643,862 | B2 | 1/2010 | Schoenefeld |
| 7,689,042 | B2 | 3/2010 | Brunner et al. |
| 7,783,008 | B2 | 8/2010 | Jabri |
| 7,949,386 | B2 | 5/2011 | Buly et al. |
| 8,014,984 | B2 | 9/2011 | Iannotti et al. |
| 8,052,623 | B2 | 11/2011 | Haimerl et al. |
| 8,090,166 | B2 | 1/2012 | Rappaport et al. |
| 8,152,816 | B2 | 4/2012 | Tuma et al. |
| 8,328,816 | B2 | 12/2012 | Beaule |
| 8,369,593 | B2 | 2/2013 | Peng et al. |
| 8,594,397 | B2 | 11/2013 | Haimerl et al. |
| 8,611,697 | B2 | 12/2013 | Nathaniel et al. |
| 8,678,125 | B2 | 3/2014 | Kosugi et al. |
| 8,679,125 | B2 | 3/2014 | Smith et al. |
| 8,694,075 | B2 | 4/2014 | Groszmann |
| 8,696,603 | B2 | 4/2014 | Takahashi et al. |
| 8,702,805 | B2 | 4/2014 | Trabish |
| 8,715,289 | B2 | 5/2014 | Smith |
| 8,774,900 | B2 | 7/2014 | Buly et al. |
| 8,828,009 | B2 | 9/2014 | Allen et al. |
| 8,831,324 | B2 | 9/2014 | Penenberg |
| 8,858,563 | B2 | 10/2014 | Philippon et al. |
| 8,888,782 | B2 | 11/2014 | Smith et al. |
| 8,890,511 | B2 | 11/2014 | Belew |
| 8,900,320 | B2 | 12/2014 | Frederick et al. |
| 8,923,584 | B2 | 12/2014 | Chabanas et al. |
| 8,934,961 | B2 | 1/2015 | Lakin et al. |
| 8,958,611 | B2 | 2/2015 | Ikits |
| 8,965,108 | B2 | 2/2015 | Chabanas et al. |
| 9,020,223 | B2 | 4/2015 | Chabanas et al. |
| 9,082,319 | B2 | 7/2015 | Shimada et al. |
| 9,113,921 | B2 | 8/2015 | Lang et al. |
| 9,113,971 | B2 | 8/2015 | Metzger et al. |
| 9,122,670 | B2 | 9/2015 | Chabanas et al. |
| 9,123,155 | B2 | 9/2015 | Cunningham et al. |
| 9,173,716 | B2 | 11/2015 | Kasodekar et al. |
| 9,183,629 | B2 | 11/2015 | Chabanas et al. |
| 9,220,567 | B2 | 12/2015 | Sutherland et al. |
| 9,271,804 | B2 | 3/2016 | Wu |
| 9,320,421 | B2 | 4/2016 | Chabanas et al. |
| 9,345,495 | B2 | 5/2016 | Gibson et al. |
| 9,345,552 | B2 | 5/2016 | Janik et al. |
| 9,386,993 | B2 | 7/2016 | Meridew et al. |
| 9,402,726 | B2 | 8/2016 | Linderman et al. |
| 9,443,346 | B2 | 9/2016 | Ikits |
| 9,480,534 | B2 | 11/2016 | Bowling et al. |
| 9,514,533 | B2 | 12/2016 | Chabanas et al. |
| 9,672,662 | B2 | 6/2017 | Scanlan et al. |
| 10,070,903 | B2 | 9/2018 | Blau |
| 10,105,168 | B2 | 10/2018 | Blau |
| 10,709,394 | B2 | 7/2020 | Zhou et al. |
| 10,918,398 | B2 | 2/2021 | Fouts et al. |
| 2003/0176783 | A1 | 9/2003 | Hu | |
| 2004/0242987 | A1* | 12/2004 | Liew | A61B 6/482 600/407 |
| 2005/0096535 | A1 | 5/2005 | de la Barrera | |
| 2007/0016008 | A1 | 1/2007 | Schoenefeld | |
| 2007/0129630 | A1 | 6/2007 | Shimko | |
| 2007/0135706 | A1 | 6/2007 | Shimko et al. | |
| 2007/0249967 | A1 | 10/2007 | Buly et al. | |
| 2007/0260256 | A1 | 11/2007 | Beaule | |
| 2008/0039717 | A1 | 2/2008 | Frigg et al. | |
| 2008/0058641 | A1 | 3/2008 | Shimko | |
| 2008/0300478 | A1 | 12/2008 | Zuhars | |
| 2009/0000626 | A1 | 1/2009 | Quaid et al. | |
| 2009/0209851 | A1 | 8/2009 | Blau | |
| 2010/0049493 | A1 | 2/2010 | Haimerl | |
| 2010/0284590 | A1 | 11/2010 | Krishnan et al. | |
| 2011/0190774 | A1 | 8/2011 | Nikolchev et al. | |
| 2011/0213374 | A1 | 9/2011 | Fitz et al. | |
| 2011/0213377 | A1 | 9/2011 | Lang et al. | |
| 2011/0213379 | A1 | 9/2011 | Blau et al. | |
| 2011/0213428 | A1 | 9/2011 | Fitz et al. | |
| 2011/0213429 | A1 | 9/2011 | Lang et al. | |
| 2011/0238431 | A1 | 9/2011 | Cionni et al. | |
| 2011/0270295 | A1 | 11/2011 | Litvack et al. | |
| 2011/0301654 | A1 | 12/2011 | Wozencroft et al. | |
| 2012/0066892 | A1 | 3/2012 | Lang et al. | |
| 2012/0271147 | A1 | 10/2012 | Kim et al. | |
| 2013/0083984 | A1 | 4/2013 | Chabanas et al. | |
| 2013/0089253 | A1 | 4/2013 | Chabanas et al. | |
| 2013/0114866 | A1 | 5/2013 | Kasodekar et al. | |
| 2013/0191099 | A1 | 7/2013 | Krekel | |
| 2013/0211232 | A1 | 8/2013 | Murphy et al. | |
| 2013/0211386 | A1 | 8/2013 | Blau et al. | |
| 2013/0211408 | A1 | 8/2013 | Kather et al. | |
| 2013/0211531 | A1* | 8/2013 | Steines | A61F 2/3859 623/20.14 |
| 2013/0314440 | A1 | 11/2013 | Simon et al. | |
| 2013/0315371 | A1 | 11/2013 | Simon et al. | |
| 2014/0079303 | A1 | 3/2014 | Pfrengle et al. | |
| 2014/0187908 | A1 | 7/2014 | Ellermann et al. | |
| 2014/0243833 | A1 | 8/2014 | Smith | |
| 2014/0278322 | A1 | 9/2014 | Jaramaz et al. | |
| 2014/0316417 | A1 | 10/2014 | Kaiser et al. | |
| 2014/0322197 | A1 | 10/2014 | Brooks | |
| 2014/0378982 | A1 | 12/2014 | Philippon et al. | |
| 2015/0066151 | A1 | 3/2015 | Frederick et al. | |
| 2015/0106024 | A1 | 4/2015 | Lightcap et al. | |
| 2015/0133945 | A1 | 5/2015 | Dushyant et al. | |
| 2015/0182295 | A1 | 7/2015 | Bozung et al. | |
| 2015/0185846 | A1 | 7/2015 | Otto et al. | |
| 2015/0265266 | A1 | 9/2015 | Sanchez et al. | |
| 2015/0265362 | A1 | 9/2015 | Andersson et al. | |
| 2015/0269727 | A1 | 9/2015 | Chabanas et al. | |
| 2015/0355298 | A1 | 12/2015 | Ben-Eliezer et al. | |
| 2016/0038160 | A1 | 2/2016 | Metzger et al. | |
| 2016/0066770 | A1 | 3/2016 | Barbato et al. | |
| 2016/0074124 | A1 | 3/2016 | Fitz et al. | |
| 2016/0113720 | A1 | 4/2016 | Lavallee et al. | |
| 2016/0135816 | A1 | 5/2016 | Lavallee et al. | |
| 2016/0157751 | A1 | 6/2016 | Mahfouz | |
| 2016/0157936 | A1 | 6/2016 | Netravali | |
| 2016/0175054 | A1 | 6/2016 | Kang et al. | |
| 2016/0191887 | A1 | 6/2016 | Casas | |
| 2016/0235381 | A1 | 8/2016 | Scanlan et al. | |
| 2016/0242931 | A1 | 8/2016 | Wong et al. | |
| 2016/0253846 | A1 | 9/2016 | Scanlan et al. | |
| 2016/0262772 | A1 | 9/2016 | Gibson et al. | |
| 2016/0278787 | A1 | 9/2016 | Axelson, Jr. et al. | |
| 2016/0278793 | A1 | 9/2016 | Meridew et al. | |
| 2016/0324580 | A1 | 11/2016 | Esterberg | |
| 2016/0331467 | A1 | 11/2016 | Slamin et al. | |
| 2017/0306416 | A1 | 10/2017 | Bedoya et al. | |
| 2018/0035964 | A1 | 2/2018 | Funabasama et al. | |
| 2018/0140309 | A1 | 5/2018 | Fouts et al. | |
| 2018/0318014 | A1 | 11/2018 | Gangwar et al. | |
| 2019/0133693 | A1 | 5/2019 | Mahfouz | |
| 2019/0167221 | A1 | 6/2019 | Simon et al. | |
| 2019/0231433 | A1 | 8/2019 | Amanatullah | |
| 2020/0253667 | A1 | 8/2020 | Fouts et al. | |

(56) References Cited

U.S. PATENT DOCUMENTS

| | | | |
|---|---|---|---|
| 2020/0312011 | A1 | 10/2020 | Kopeinigg et al. |
| 2021/0169503 | A1 | 6/2021 | Fouts et al. |
| 2021/0259774 | A1 | 8/2021 | Fouts et al. |
| 2022/0183760 | A1 | 6/2022 | Fouts et al. |

FOREIGN PATENT DOCUMENTS

| | | | |
|---|---|---|---|
| CN | 104185451 A | 12/2014 | |
| CN | 104244860 A | 12/2014 | |
| CN | 112037200 A | 12/2020 | |
| DE | 10057023 A1 | 6/2002 | |
| EP | 1844726 B1 | 10/2007 | |
| EP | 2618313 A1 | 7/2013 | |
| WO | 2011/158117 A2 | 12/2011 | |
| WO | 2012/149964 A1 | 11/2012 | |
| WO | 2013/174401 A1 | 11/2013 | |
| WO | 2013/174402 A1 | 11/2013 | |
| WO | 2014/048447 A1 | 4/2014 | |
| WO | 2015/124171 A1 | 8/2015 | |
| WO | 2016/154557 A1 | 9/2016 | |
| WO | 2017218933 A1 | 12/2017 | |

OTHER PUBLICATIONS

Alignment Disorders, Radiology Key, 2015, https://radiologykey.com/alignment-disorders/.

Allen, D. et al., Prevalence of associated deformities and hip pain in patients with cam-type femoroacetabular impingement, J Bone Joint Surg, vol. 91-B. No. 5, May 2009, pp. 589-594.

Anderson, Lucas A. et al., Acetabular Carilage Delamination in Femoroacetabular Impingement: Risk Factors and Magnetic Resonance Imaging Diagnosis, J Bone Joint Surg Am, vol. 91, No. 2009, pp. 305-313.

Atlas of MSK Measurements: how to draw the alpha angle, Stanford MSK, http://xrayhead.com/measure/show_measurement.php?i=3.

Atlas of MSK Measurements: how to draw the femoral version, Stanford MSK, http://xrayhead.com/measure/show_measurement.php?i=5.

Audenaert et al. (May 2012). "Imageless versus image-based registration in navigated arthroscopy of the hip," The Journal of Bone & Joint Surgery 94-B(5) 624-629.

Audenaert, Emmanuel A. et al., Development of a three-dimensional detection method of cam deformities in femoroacetabular impingement, Skeletal Radiology, vol. 40, 2011, pp. 921-927.

Audenaert, Emmanuel A. et al., Three-Dimensional Assessment of Cam Engagement in Femoroacetabular Impingement, Arthroscopy, vol. 27, No. 2, 2011, pp. 167-171.

Beaule, Paul E. et al., Three-dimensional computed tomography of the hip in the assessment of femoroacetabular impingement, J Orthop Res, vol. 23, 2005, pp. 1286-1292.

Beck, M. et al., Hip morphology influences the pattern of damage to the acetabular cartilage: femoroacetabular impingement as a cause of early osteoarthritis of the hip, J Bone Joint Surg, vol. 87-B, No. 7, 2005, pp. 1012-1018.

Bei, Yanhong. et al., Multibody dynamic simulation of knee contact mechanics, Med Eng Phys., vol. 26, No. 9, Nov. 2004, pp. 777-789.

Bouma, Heinse W. et al., Can Combining Femoral and Acetabular Morphology Parameters Improve the Characterization of Femoroacetabular Impingement?, Clin Orthop Rel Res, vol. 473, No. 4, 2015, pp. 1396-1403.

Broughton, N. S. et al., Reliability of radiological measurements in the assessment of the child's hip, J Bone Joint Surg, vol. 71-B, No. 1, 1989, p. 6-8.

Butler, Mark H., Current Technologies for Device Independence, Hewlett Packard, 2001, pp. 1-28.

Cadet, Edwin R. et al., Inter- and intra-observer agreement of femoroacetabular impingement (FAI) parameters comparing plain radiographs and advanced, 3D computed tomographic (CT)-generated hip models in a surgical patient cohort, Knee Surg Sports Traumatol Arthrosc, vol. 27, No. 7, 2014, pp. 2324-2331.

Carlisle, John C. et al., Reliability of Various Observers in Determining Common Radiographic Parameters of Adult Hip Structural Anatomy, The Iowa Orthopaedic Journal, vol. 31, 2011, pp. 52-58.

Chadayammuri, Vivek et al., Measurement of lateral acetabular coverage: a comparison between CT and plain radiography, J Hip Preservation Surgery, vol. 2, No. 4, Oct. 22, 2015, pp. 392-400.

Chadayammuri, Vivek et al., Passive Hip Range of Motion Predicts Femoral Torsion and Acetabular Version, J Bone Joint Surg Am., vol. 98, 2016, pp. 127-134.

Chavhan, Govind B. et al., Principles, Techniques, and Applications of $T2^*$-based MR Imaging and Its Special Applications, RadioGraphics, vol. 29, 2009, pp. 1433-1449.

Cheng, Hui et al., Comparison of 2.5D and 3D Quantification of Femoral Head Coverage in Normal Control Subjects and Patients with Hip Dyplasia, PLOS One, vol. 10, No. 11, Nov. 24, 2015, pp. 1-14.

Clohisy, John C. et al., A Systematic Approach to the Plain Radiographic Evaluation of the Young Adult Hip, J Bone Joint Surg Am., vol. 90, Supp. 4, 2008, pp. 47-66.

Clohisy, John C. et al., Radiographic Evaluation of the Hip has Limited Reliability, Clin Orthop Relat Res, vol. 467, 2009, pp. 666-675.

Clohisy, John C. et al., The Frog-leg Lateral Radiograph Accurately Visualized Hip Cam Impingement Abnormalities, Clin Orthop Relat Res, No. 462, Sep. 2007, pp. 115-121.

Cobb et al. (Apr. 30, 2010). "Cams and Pincer Impingement Are Distinct, Not Mixed," Clinical Orthopaedics and Related Research 468(8): 2143-2151.

Dandachli, W. et al., Analysis of cover of the femoral head in normal and dysplastic hips, J Bone Joint Surg, vol. 90- B, No. 11, 2008, pp. 1428-1434.

Dandachli, W. et al., Three-dimensional CT analysis to determine acetabular retroversion and the implications for the management of femoro-acetabular impingement, J Bone Joint Surg. vol. 91-B, No. 8, 2009, pp. 1031-1036.

Danz, J.C. et al., Three-dimensional portable document format: A simple way to present 3-dimensional data in an electronic publication, American Journal of Orthodontics and Dentofacial Orthopedics, vol. 140, No. 2, Aug. 2011, pp. 274-276.

Decision of Rejection dated Sep. 1, 2022, directed to CN Application No. 201780083846.8; 14 pages.

Dyonics Plan Hip Impingement Planning System: User Manual and Frequently Asked Questions, Smith & Nephew, Inc., 2014.

Eguizabal, Alma et al., A Weighting Strategy for Active Shape Models, IEEE International Conference on Image Processing, 2017.

Eijer, H. et al., Evaluation and Treatment of Young Adults with Femoro-Acetabular Impingement Secondary to Perthes' Disease, Hip Int., vol. 16, No. 4, 2006, pp. 273-280.

EOS Imaging. "EOS System," located at https://www.eos-imaging.com/us/our-expertise/imaging-solutions/eos-system, visited on Oct. 29, 2019. 8 pages.

Extended European Search Report dated May 13, 2020, directed to EP Application No. 17870894.7; 12 pages.

Fa, Lianggluo et al., Superiority of the modified Tonnis angle over the Tonnis angle in the radiographic diagnosis of acetabuular dysplasia, Experimental and Therapeutic Medicine, vol. 8, 2014, pp. 1934-1938.

Fabricant, Peter D. et al., Clinical Outcomes After Arthroscopic Psoas Lengthening: The Effect of Femoral Version, Arthroscopy, vol. 28, No. 7, 2012, pp. 965-971.

Fabricant, Peter D. et al., The Effect of Femoral and Acetabular Version on Clinical Outcomes After Arthroscopic Femoroacetabular Impingement Surgery, J Bone Joint Surg, vol. 97, No. 7, 2015, pp. 537-543.

First Office Action dated Aug. 31, 2021, directed to CN Application No. 201780083846.8; 25 pages.

Fouts et al., U.S. Notice of Allowance and Fee(s) Due mailed Nov. 3, 2022, directed to U.S. Appl. No. 17/143,091; 9 pages.

Fouts et al., U.S. Notice of Allowance and Fee(s) Due mailed Oct. 8, 2020, directed to U.S. Appl. No. 15/818,394; 7 pages.

Fouts et al., U.S. Office Action dated Apr. 21, 2020, directed to U.S. Appl. No. 15/818,394; 33 pages.

(56) References Cited

OTHER PUBLICATIONS

Fouts et al., U.S. Office Action dated Dec. 20, 2019, directed to U.S. Appl. No. 15/818,394: 28 pages.
Fouts et al., U.S. Office Action dated Feb. 15, 2019, directed to U.S. Appl. No. 15/818,394; 21 pages.
Fouts et al., U.S. Office Action dated Mar. 1, 2022, directed to U.S. Appl. No. 16/785,367; 31 pages.
Fouts et al., U.S. Office Action dated Mar. 23, 2023, directed to U.S. Appl. No. 16/785,367; 18 pages.
Fouts et al., U.S. Office Action dated Nov. 9, 2023, directed to U.S. Appl. No. 18/190,956; 18 pages.
Fouts et al., U.S. Office Action dated Sep. 23, 2022, directed to U.S. Appl. No. 16/785,367; 21 pages.
Gosvig, K. K. et al., A new radiological index for assessing asphericity of the femoral head in cam impingement, J Bone Joint Surg, vol. 89-B, No. 10, Oct. 2007, pp. 1309-1316.
Hanson, Joey A. et al., Discrepancies in measuring acetabular coverage: revisiting the anterior and lateral center edge angels, Journal of Hip Preservation Surgery, vol. 2, No. 3, 2015, pp. 280-286.
Hellman, Michael D. et al., Radiographic Comparison of Anterior Acetabular Rim Morphology Between Pincer Femoroacetabular Impingement and Control, Arthroscopy, vol. 32, No. 3, 2016, pp. 468-472.
Hernandez, Ramiro J. et al., CT Determination of Femoral Torsion, AJR, vol. 137, Jul. 1981, pp. 97-101.
Hetsroni, Iftach et al., Anterior Inferior Illiac Spine Morphology Correlates With Hip Range of Motion: A Classification System and Dtynamic Model, Clin Orthop Relat Res, vol. 471, No. 8, Aug. 2013, pp. 2497-2503.
Heyworth, Benton E. et al., Preoperative Three-dimensional CT Predicts Intraoperative Findings in Hip Arthroscopy, Clin Orthop Rlat Res, vol. 470, No. 7, Jul. 2012, pp. 1950-1957.
International Preliminary Report on Patentability dated Aug. 23, 2022, directed to International Application No. PCT/US2021/018911; 10 pages.
International Preliminary Report on Patentability mailed on May 31, 2019 for PCT Application No. PCT/US2017/062603 filed Nov. 20, 2017, 11 pages.
International Search Report and Written Opinion mailed Jun. 1, 2021, directed to International Application No. PCT/US2021/018911; 17 pages.
International Search Report and Written Opinion mailed May 10, 2022, directed to International Application No. PCT/US2021/072917; 13 pages.
International Search Report and Written Opinion mailed on Feb. 1, 2018 for PCT Application No. PCT/US2017/062603 filed Nov. 20, 2017, 12 pages.
Ito, K. et al., Femoroacetabular impingement and the cam-effect: a MRI-based quantitative anatomical study of the femoral head-neck offset, J Bone Joint Surg, vol. 83-B, No. 2, Mar. 2001, pp. 171-176.
Jesse, Mary Kristen et al., Normal Anatomy and Imaging of the Hip: Emphasis on Impingement Assessment, Seminars in Musculoskeletal Radiology, vol. 17, No. 3, 2013, pp. 229-247.
Johnston, Todd L. et al., Relationship Between Offset Angle Alpha and Hip Chondral Injury in Femoroacetabular Impingement, Arthoroscopy, vol. 24, No. 6, 2008, pp. 669-675.
Kasten et al. (Apr. 2020). "End-To-End Convultional Neural Network for 3D Reconstruction of Knee Bones from Bi-Planar X-Ray Images," 12 pages.
Kelkar, Rajeev, Normal and Abnormal Mechanics of the Shoulder: Studies of Articular Geometry, Contact, and Kinematics, ProQuest Dissertations and Theses, 1996.
Kelly, Bryan T. et al., Alterations in Internal Rotation and Alpha Angles Are Associated With Arthroscopic Cam Decompression in the Hip, The American Journal of Sports Medicine, 2012, pp. 1-6.
Konishi, N. et al., Determination of acetabular coverage of the femoral head with use of a single anteroposterior radiograph. A new computerized technique, J Bone Joint Surg Am, vol. 75-A, No. 9, 1993, pp. 1318-1333.
Kraeutler, Matthew J. et al., Femoral Version Abnormalities Significantly Outweigh Effect of Cam Impingement on Hip Internal Rotation, J Bone Joint Surg Am., vol. 100-A, No. 3, 2018, pp. 205-210.
Krekel, P.R. et al., Interactive simulation and comparative visualisation of the bone-determined range of motion of the human shoulder, SimVis, 2006, pp. 1-13.
Laborie, Lene Bjerke et al., Radiographic measurements of hip dysplasia at skeletal maturity—new reference intervals baed on 2,036 19 -yea-old Norwegians, Skeletal Radiol, vol. 42, No. 7, Jul. 2013, pp. 925-935.
Lambers et al., U.S. Advisory Action dated Oct. 21, 2021, directed to U.S. Appl. No. 16/261,464; 5 pages.
Lambers et al., U.S. Notice of Allowance and Fee(s) Due mailed May 13, 2022, directed to U.S. Appl. No. 16/261,464; 5 pages.
Lambers et al., U.S. Office Action dated Dec. 15, 2020 directed U.S. Appl. No. 16/261,464; 16 pages.
Lambers et al., U.S. Office Action dated Dec. 20, 2021, directed to U.S. Appl. No. 16/261,464; 15 pages.
Lambers et al., U.S. Office Action dated Jun. 11, 2021, directed to U.S. Appl. No. 16/261,464; 13 pages.
Larson, Christopher M. et al., Are Normal Hips Being Labeled as Pathologic? A CT-based Method for Defining Normal Acetabular Coverage, Clin Orthop Relat Res, vol. 473, No. 4, Apr. 5, 2015. pp. 1247-1254.
Larson, Christopher M. et al., Arthroscopic Hip Revision Surgery for Residual Femoroacetabular Impingement (FAI): Surgical Outcomes Compared With a Matched Cohort After Primary Arthroscopic FAI Correction, The Am J of Sports Med. vol. 42, No. 8, 2014, pp. 1785-1790.
Leboeuf, Fabien, Using LATEX to produce multi-media clinical reports, The PracTeX Journal, No. 1, 2011, pp. 1-14.
Lequesne, M. et al., The normal hip joint space: variations in width, shape, and architecture on 223 pelvic radiographs, Ann Rheum Dis, vol. 63, 2004, pp. 1145-1151.
Levy, David M. et al., Prevalence of Cam Morphology in Females with Femoroacetabular Impingement, Front. Surg., vol. 2, No. 61, Dec. 2015, pp. 1-5.
Linder et al. (Aug. 2013). "Fully Automatic Segmentation of the Proximal Femur Using Random Forest Regression Voting," IEEE Transactions on Medical Imaging 32(8):1462-1472.
Mardones, Rodrigo M. et al., Surgical Correction of "Cam-Type" Femoroacetabular Impingement: A Cadaveric Comparison of Open Versus Arthroscopic Debridement, Arthroscopy, vol. 25, No. 2, 2009, pp. 175-182.
Mardones, Rodrigo M. et al., Surgical Treatment of Femoroacetabular Impingement: Evaluation of the Effect of the Size of the Resection, J Bone Joint Surg Am, vol. 88A, Supp. 1, Mar. 2006, pp. 84-91.
Matsuda et al., Acute Iatrogenic Dislocation Following Hip Impingement Arthroscopic Surgery, Arthroscopy, vol. 25, No. 4, 2009, pp. 400-404.
Matsuda et al., Closed Intramedullary Derotational Osteotomy and Hip Arthroscopy for Cam Femoroacetabular Impingement From Femoral Retroversion, Arthroscopy Techniques, vol. 3, No. 1, 2014, pp. e83-e88.
McCarthy, Joseph et al., Anatomy, pathologic features, and treatment of acetabular labral tears, Clin Orthop Relat Res, No. 406, 2003, pp. 38-47.
Meyer, Dominik C. et al., Comparison of Six Radiographic Projections to Assess Femoral Head/Neck Ashpericity, Clin Orthop Relat Res. No. 445, 2006, pp. 181-185.
Milone, Michael T. et al., Novel CT-based Three-dimensional Software Improves the Characterization of Cam Morphology, Clin Orthop Relat Res, vol. 471, No. 8, Aug. 2013, pp. 2484-2491.
Minciullo et al. "Fully Automated Shape Analysis for Detection of Osteoarthritis from Lateral Knee Radiographs," 2016 23rd International Conference on Pattern Recognition (ICPR), Dec. 4-8, 2016, Cancún Center, Cancún, México; pp. 3787-3791.
Miyasaka, Dai et al., Three-dimensional Assessment of Femoral Head Coverage in Normal and Dysplastic Hips: A Novel Method, Acta Med., vol. 68, No. 5, 2014, pp. 277-284.

(56) References Cited

OTHER PUBLICATIONS

Murphy, S.B. et al., The prognosis in untreated dysplasia of the hip: A study of radiographic factors that predict the outcome, J Bone Joint Surg Am, vol. 77-A, No. 7, 1995, pp. 985-989.
Nepple, Jeffrey J. et al., Clinical and Radiographic Predictors of Intra-articular Hip Disease in Arthroscopy, Am J Sports Med, vol. 39, No. 2, 2011, pp. 296-303.
Nepple, Jeffrey J. et al., Diagnostic Imaging of Femoroacetabular Impingement, J Am Acad Orthop Surg, vol. 21, Suppl. 1, 2013, pp. S20-S26.
Nepple, Jeffrey J. et al., Do Plain Radiographs Correlate With CT for Imaging of Cam-type Femoroacetabular Impingement ?, Clin Orthop Relat Res, vol. 470, No. 12, Dec. 2012, pp. 3313-3320.
Notzli, H.P. et al., The contour of the femoral head-neck junction as a predictor for the risk of anterior impingement, J Bone Joint Surg, vol. 84-B, 2002, pp. 556-560.
Office Action dated Aug. 23, 2023, directed to EP Application No. 17 870 894.7; 6 pages.
Ogata, S. et al., Acetabular cover in congenital dislocation of the hip, J Bone Joint Surg, vol. 72-B, No. 2, 1990, pp. 190-196.
Omeroglu, Hakan et al., Analysis of a radiographic assessment method of acetabular cover in developmental dysplasia of the hip, Arch Orthop Trauma Surg, vol. 122, No. 6, 2002, pp. 334-337.
Omeroglu, Hakan et al., Measurement of center-edge angle in developmental dysplasia of the hip: a comparison of two methods in patients under 20 years of age, Skeletal Radiol, vol. 31, No. 1, 2002, pp. 25-29.
Outerbridge, R.E., The etiology of chondromalacia patellae, J Bone Joint Surg, vol. 43-B, No. 4, 1961, pp. 556-560.
Ozcelik, Abdurrahman et al., Definition of a quantitative measurement method for acetabular version in a plain radiograph in the healthy adult hip, Eklem Hastalik Cerrahisi, vol. 26, No. 1, 2015, pp. 2-5.
Panoramic Fluoro, Radlink Inc., 2017, http:--www.radlink.com-index.php-products-software-surgeons-checklist-software-panoramic-fluoro-.
Perreira, Aimee C. et al., Multilevel Measurement of Acetabular Version Using 3-D CT-generated Models, Clin Orthop Relat Res, vol. 469, No. 2, Feb. 2011, pp. 552-561.
Phelps, A. et al., Embedding 3D Radiology Models in Portable Document Format, American Journal of Roentgenology, vol. 199, No. 6, Dec. 2012, pp. 1342-1344.
Rakhra, Kawan S. et al., Comparison of MRI Alpha Angle Measurement Planes in Femoroacetabular Impingement, Clin Orthop Relat Res, vol. 467, No. 3, 2009, pp. 660-665.
Reikeras, Olav et al., Cross table lateral radiography for measurement of acetabular cup version, Ann Transl Med., vol. 4, No. 9, 2016, pp. 1-4.
Reynolds, D. et al., Retroversion of the acetabulum: a cause of hip pain, J Bone Joint Surg, vol. 81-B, No. 2, Mar. 1999, pp. 281-288.
Ross, James R. et al., Intraoperative Fluoroscopic Imaging to Treat Cam Deformities: Correlation With 3-Dimensional Computed Tomography, Am J. Sports Med. vol. 42, No. 6, 2014, pp. 1370-1376.
Ruthensteiner, B. et al., Embedding 3D Models of Biological Specimens in PDF Publications, Microscopy Research and Technique, vol. 71, No. 11, 2008, pp. 778-786.
Schumann et al. (2013). "An Integrated System for 3D Hip Joint Reconstruction from 2D X-rays: A Preliminary Validation Study," Annals of Biomedical Engineering, 41(10): 2077-2087.
Second Office Action dated Mar. 16, 2022, directed to CN Application No. 201780083846.8; 17 pages.
Siebenrock, K.A. et al., Effect of Pelvic Tilt on Acetabular Retroversion: A Study of Pelves From Cadavers, Clin Orthop Relat Res. No. 407, Feb. 2003, pp. 241-248.
Stahelin, Lisca et al., Arthroscopic Offset Restoration in Femoroacetabular Cam Impingement: Accuracy and Early Clinical Outcome, Arthroscopy: The J of the Arthroscopic and Rel Surg, vol. 24, No. 1, 2008, pp. 51-57.
Stelzeneder, David et al., Can Radiographic Morphometric Parameters for the Hip Be Assessed on MRI?, Clin Orthop Relat Res, vol. 471, No. 3, Mar. 2013, pp. 989-999.
Stubbs, Allston J. et al., Classic measures of hip dysplasia do not correlate with three-dimensional computer tomographic measures and indices, Hip Int, vol. 21, No. 5, 2011, pp. 549-558.
Tannast, Moritz et al., Conventional radiographs to assess femoroacetabular impingement, Instr Course Lect, vol. 58, 2009, pp. 203-212.
Tannast, Moritz et al., Femoroacetabular Impingement: Radiographic Diagnosis—What the Radiologist Should Know, Am J Radiology, vol. 188, Jun. 2007, pp. 1540-1552.
Tannast, Moritz et al., Noninvasive Three-Dimensional Assessment of Femoroacetabular Impingement, J Orthop Res, vol. 25, No. 1, 2007, pp. 122-131.
Tannast, Moritz et al., Which Radiographic Hip Parameters Do Not Have to Be Corrected for Pelvic Rotation and Tilt?, Clin Orthop Relat Res, vol. 473, No. 4, Apr. 2015, pp. 1255-1266.
Tannenbaum, Eric et al., Gender and racial differences in focal and global acetabular version, J Arthroplasty, vol. 29, No. 2, Feb. 2014, pp. 373-376.
Tannenbaum, Eric P. et al., A Computed Tomography Study of Gender Differences in Acetabular Version and Morphology: Implications for Femoroacetabular Impingement, The J of Arthroscopic and Rel Surg, vol. 31, No. 7, 2015, pp. 1247-1254.
Thaler et al. "Volumetric Reconstruction from a Limited Number of Digitally Reconstructed Radiographs Using CNNs," Proceedings of a OAGM Workshop, 2018; pp. 13-19.
Tonnis, D. et al., Acetabular and Femoral Anteversion: Relationship with Osteoarthritis of the Hip, J Bone Joint Surg Am, vol. 81-A, No. 12, 1999, pp. 1747-1770.
Tonnis, D., Congenital Dysplasia and Dislocation of the Hip in Children and Adults, Chapter 9, 1987, pp. 100-142.
Uchida, Soshi et al., Clinical and Radiographic Predicators for Worsened Clinical Outcomes After Hip Arthroscopic Labral Preservation and Capsular Closure in Developmental Dysplasia of the Hip, Am J Sports Med. vol. 44, No. 1, 2016, pp. 28-38.
Van Bosse, Harold J. P. et al., Pelvic Positioning Creates Error in CT Acetabular Measurements, Clin Orthop Relat Res, vol. 469, No. 6, Jun. 2011, pp. 1683-1691.
Werner, Clement M. L. et al., Normal values of Wiberg's lateral center-edge angle and Lequesne's acetabular index-a coxometric update, Skeletal Radiol, vol. 41, 2012, pp. 1273-1278.
Wiberg, Gunnar, Studies on Dysplastic Acetabula and Congenital Subluxation of the Hip Joint with Special Reference to the Complication of Osteoarthritis, Orthopedic Clinic of Karolinska Institutet, 1939, pp. 1-39 and 129-135.
Wilson, J. D. et al., To what degree is digital imaging reliable? Validation of femoral neck shaft angle measurement in the era of picture archiving and communication systems, The British Journal of Radiology, vol. 84, Apr. 2011, pp. 375-379.
Zaltz, Ira et al., The Crossover Sign Overestimates Acetabular Retroversion, Clin Orthop Relat Res, vol. 471, 2013, pp. 2463-2470.
Zhao et al. "Automated Analysis of Femoral Artery Calcification Using Machine Learning Techniques," 2019 International Conference on Computational Science and Computational Intelligence (CSCI), Dec. 5-7, 2019, Las Vegas, Nevada, United States; pp. 584-589.
Ziegler, A. et al., Effectively incorporating selected multimedia content into medical publications, BMC Medicine, vol. 9, No. 17, 2011, pp. 1-6.

\* cited by examiner

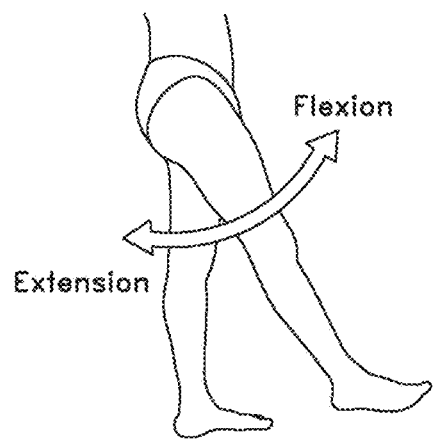
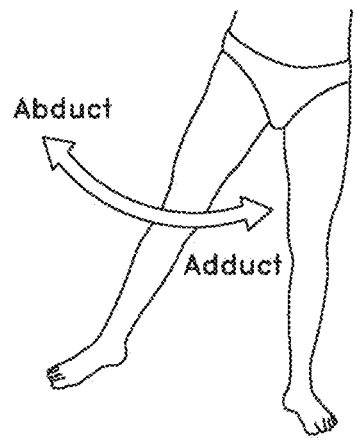
FIG. 1A   FIG. 1B
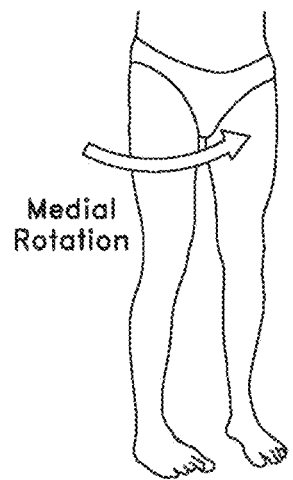
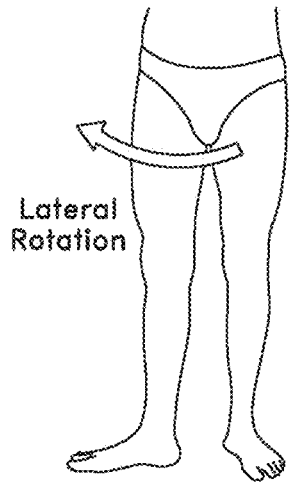
FIG. 1C   FIG. 1D

CAM-TYPE FEMOROACETABULAR IMPINGEMENT (FAI)

A

CAM INJURY TO THE LABRUM

B

PINCER-TYPE FEMOROACETABULAR IMPINGEMENT (FAI)

PINCER INJURY TO THE LABRUM

SYSTEMS AND METHODS FOR PRE-OPERATIVE VISUALIZATION OF A JOINT

CROSS-REFERENCE TO RELATED APPLICATIONS

This application is a continuation of U.S. patent application Ser. No. 16/261,464, filed Jan. 29, 2019, which claims the benefit of U.S. Provisional Application No. 62/623,068, filed Jan. 29, 2018, the entire contents of each of which are hereby incorporated herein by reference.

FIELD OF THE INVENTION

This invention generally relates to orthopedics, and more particularly to pre-operative planning for orthopedic procedures.

BACKGROUND OF THE INVENTION

Orthopedics is a medical specialty that focuses on the diagnosis, correction, prevention, and treatment of patients with skeletal conditions, including for example conditions or disorders of the bones, joints, muscles, ligaments, tendons, nerves and skin, which make up the musculoskeletal system. Joint injuries or conditions such as those of the hip joint or other joints can occur from overuse or over stretching or due to other factors, including genetic factors, and may cause deviation from the baseline anatomy of the joint.

The hip joint movably connects the leg to the torso. The hip joint is a ball-and-socket joint, and is capable of a wide range of different motions, e.g., flexion and extension, abduction and adduction, internal (medial) and external (lateral) rotation, etc. These motions are illustrated in FIGS. 1A-1D. The hip joint is formed at the junction of the femur and the hip. More particularly, and with reference to FIG. 2, the ball of the femur is received in the acetabular cup of the hip, with a plurality of ligaments and other soft tissue serving to hold the bones in articulating condition.

The hip joint is susceptible to a number of different pathologies (e.g., conditions or disorders). These pathologies can have both congenital and injury-related origins. One type of pathology of the hip joint involves impingement between the femoral head and/or femoral neck and the rim of the acetabular cup. This impingement is sometimes referred to as femoroacetabular impingement (FAI). In some cases, and with reference to FIG. 3, FAI impingement can occur due to irregularities in the geometry of the femur (e.g., due to an excess of bone on the femur). This type of impingement is sometimes referred to as cam-type FAI. In other cases, and with reference to FIG. 4, the FAI impingement can occur due to irregularities in the geometry of the acetabular cup (e.g., due to an excess of bone on the acetabular cup). This latter type of impingement is sometimes referred to as pincer-type FAI. In still other cases, the impingement may be due to irregularities in the geometry of both the femur and the acetabulum (e.g., an excess of bone on both the femur and the acetabular cup). This type of impingement is sometimes referred to as mixed-type FAI. In all of these cases, the salient feature of the impingement is that the bone of the femur and acetabulum approach and impinge on one another and any intermediary soft tissues during "normal" articulation of the hip joint.

FAI can result in a reduced range of motion, substantial pain and, in some cases, significant deterioration of the hip joint. In some cases, the FAI may be sufficiently severe as to require surgical intervention, e.g., removal of the bone causing the FAI and repair of any damaged soft tissues.

A current trend in orthopedic surgery is to treat joint pathologies using minimally-invasive arthroscopic techniques, for example, "keyhole" surgery conducted through small portals in the skin, with the surgical site being visualized with arthroscopes. However, when treating FAI using minimally-invasive arthroscopic techniques, it is generally quite difficult for the physician to determine exactly how much bone should be removed, and whether the shape of the remaining bone has a desired geometry. In practice, physicians tend to err on the side of caution and remove less bone rather than more bone. Significantly, under-resection of the pathology is the leading cause of revision hip arthroscopy.

Therefore, it is desirable to provide the physician with improved guidance with respect to the extent of the pathology, and how much bone should be removed, when treating FAI using minimally-invasive arthroscopic techniques.

With regard to the hip joint, for example, two common anatomical measurements used in assessing FAI are: (i) the Alpha Angle for cam-type impingement, and (ii) the Lateral Center Edge Angle for pincer-type impingement. These two measurements are typically obtained by analyzing pre-operative images (e.g., pre-operative X-ray images), with the two measurements providing a measure of the degree to which the patient's hip anatomy deviates from normal, healthy hip anatomy.

To measure the Alpha Angle, and with reference to FIG. 5, the surgeon manually draws a best-fit circle 5 over the femoral head 10 so that the perimeter of the circle matches the perimeter of the femoral head as closely as possible. The surgeon then manually draws a line 15 along the mid-line of the femoral neck 20. The surgeon then manually draws a second line 25 which originates at the center of the femoral head and passes through the location which signifies the start of the cam pathology 30 (i.e., the location where the bone first extends outside the circle 5 set around the femoral head 10). The surgeon then measures the angle 35 between the two lines 15, 25: this angle is the patient's Alpha Angle 35. An Alpha Angle of greater than 42 degrees is typically indicative of a cam deformity, and an Alpha Angle of greater than 55 degrees is typically indicative of a clinically-significant impingement leading to a decreased range of motion compared to a normal hip.

To measure the Lateral Center Edge Angle, and with reference to FIG. 6, the surgeon manually draws a vertical line 40 which originates at the center of the femoral head 10 and is perpendicular to the horizontal axis and then manually draws a second line 45 which originates at the center of the femoral head and passes through the location which signifies the start of the pincer pathology 50 (i.e., the rim of the acetabular cup). The surgeon then measures the angle 55 between the two lines 40, 45: this angle is the patient's Lateral Center Edge Angle. A Lateral Center Edge Angle of between 20-25 degrees is typically indicative of borderline undercoverage and may result in hip instability, a Lateral Center Edge Angle of less than 20 degrees is typically indicative of hip dysplasia, and a Lateral Center Edge Angle of greater than 40 degrees is typically indicative of over-coverage (pincer-type FAI) and may result in hip impingement and a decreased range of motion.

Two other measurements which are helpful in assessing the extent to which the patient's hip anatomy deviates from normal, healthy hip anatomy are: (i) Acetabular Version, and (ii) Femoral Torsion.

Acetabular Version is measured as the angle 60 (FIG. 7) between the sagittal plane 65 (perpendicular to the frontal plane, not shown, and perpendicular to the horizontal axis 70) and a line 75 that connects the posterior and anterior aspects of the acetabular rim on a transverse plane. Acetabular version of 15-20 degrees is generally considered normal, while acetabular anteversion greater than 25 degrees is considered indicative of anterior undercoverage and may result in hip instability. Acetabular retroversion (i.e.: acetabular version less than 15 degrees) can be indicative of posterior superior undercoverage or anterior overcoverage and may result in hip instability, or hip impingement, or both.

Femoral Torsion is measured as the projected (axial) angle 80 (FIG. 8) between the femoral neck axis 85 and the condylar axis 90 and incorporates both neck inclination and femoral shaft rotation. Femoral torsion of 10-20 degrees is considered normal, while femoral torsion of greater than 25 degrees is considered pathologic and may result in hip instability. Femoral torsion of less than 5 degrees is considered pathologic and may result in hip impingement.

SUMMARY OF THE INVENTION

According to some embodiments, pre-operative joint visualization systems and methods are provided for assisting a physician in planning for a surgical procedure to address a joint pathology (e.g., a joint condition or disorder). According to some embodiments, visualizations can provide guidance with respect to the extent of the pathology and how much bone should be removed during a surgical procedure using, for example, minimally-invasive arthroscopic techniques or open surgical procedures.

According to some embodiments, patient-specific and/or patient population information is obtained, preferably via a 3D imaging process. For example, a patient's hip joint (e.g., the femoral head, the femoral neck and the acetabular cup), pelvis, and femoral condyles may be scanned with an imaging apparatus (e.g., a CT scanner, an MRI scanner, etc.) and the imaging data may used to build a virtual 3D model of the patient's hip joint. The virtual 3D model may then be analyzed to generate a set of patient-specific measurements that are associated with a planned surgery (e.g., Alpha Angle calculations for cam-type FAI procedures, Lateral Center Edge Angle calculations for pincer-type FAI procedures, measurements of Acetabular Version and Femoral Torsion, etc.). In some embodiments, the virtual 3D model may be analyzed with reference to a baseline anatomy derived, for example, from data from a patient population.

According to some embodiments, patient-specific measurements may be integrated into a virtual 3D rendering of the 3D model. In some embodiments, additional virtual objects that are representative of the patient-specific measurements may be integrated into the virtual 3D rendering. Images may be generated that graphically illustrate important measurement and morphology features relating to an FAI lesion and proper resection of the FAI lesion.

According to some embodiments, a physician can be provided with information (including measurements and visualizations) on the extent of a pathology, and how much bone should be removed, in order to restore normal morphology, and information (including measurements and visualizations) about the bone, such as for treating FAI using minimally-invasive arthroscopic techniques or an open surgical procedure.

According to some embodiments, a method for visualizing at least one region of a joint that deviates from a baseline anatomy for a surgical procedure on the at least one region of the joint includes receiving image data associated with a joint of a subject, generating a three-dimensional model of at least a portion of the joint of the subject using the image data, identifying at least one region of the joint that deviates from the baseline anatomy by comparing at least a portion of the three-dimensional model to a baseline model, generating a measurement of a characteristic of the joint at one or more predefined locations using the three-dimensional model and a coordinate system, and generating a three-dimensional rendering of the model, wherein the three-dimensional rendering comprises: a visual indication of the at least one region of the three-dimensional model that deviates from the baseline, wherein the at least one region is visually indicated according to degree of deviation, and a representation of the measurement of the characteristic of the joint that is positioned in the rendering according to the one or more predefined locations.

In any of these embodiments, the image data can include at least one of an MM scan and a CT scan.

In any of these embodiments, the three-dimensional rendering can include a visual indication of the coordinate system.

In any of these embodiments, the coordinate system can include clock-face lines.

In any of these embodiments, the representation of the measurement can be provided adjacent to a clock-face line.

In any of these embodiments, the visual indication of the at least one region can be a heat map.

In any of these embodiments, the heat map can indicate an amount of tissue to remove to match the baseline anatomy.

In any of these embodiments, the joint can be a hip joint and the measurement of the characteristic can include at least one of an alpha angle and a lateral center edge angle.

In any of these embodiments, the joint can be a hip joint and the deviation from the baseline can be associated with at least one of a cam-type impingement and a pincer-type impingement.

In any of these embodiments, the three-dimensional rendering can include at least one indication of a location of a threshold characteristic value in the rendering.

In any of these embodiments, the at least one indication can include a curve connecting points that meet the threshold characteristic value.

In any of these embodiments, the joint can be a hip joint, the characteristic can be an alpha angle, and the threshold characteristic value can be 55 degrees, 65 degrees, or 75 degrees.

In any of these embodiments, the method may further include displaying a spectrum bar graph that comprises the representation of the measurement of the characteristic of the joint, wherein regions of the spectrum bar graph are visually-coded to indicate normal and abnormal anatomical measurement ranges.

In any of these embodiments, the method may further include displaying a coordinate system value that is associated with the representation of the measurement.

In any of these embodiments, the method may further include displaying a representation of at least a portion of a resection tool and visually coding the representation to indicate a dimension of the at least a portion of the resection tool, wherein the visual coding is coordinated with the visual indication of the at least one region of the three-dimensional model that deviates from the baseline.

According to some embodiments, a system for generating a visualization of at least one region of a joint that deviates from a baseline anatomy for a surgical procedure on the at least one region of the joint, the system comprising one or more processors, memory, and one or more programs, wherein the one or more programs are stored in the memory and configured to be executed by the one or more processors, the one or more programs including instructions for: receiving image data associated with a joint of a subject; generating a three-dimensional model of at least a portion of the joint of the subject using the image data; identifying at least one region of the joint that deviates from the baseline anatomy by comparing at least a portion of the three-dimensional model to a baseline model; generating a measurement of a characteristic of the joint at one or more predefined locations using the three-dimensional model and a coordinate system; and generating a three-dimensional rendering of the model, wherein the three-dimensional rendering comprises: a visual indication of the at least one region of the three-dimensional model that deviates from the baseline, wherein the at least one region is visually indicated according to degree of deviation, and a representation of the measurement of the characteristic of the joint that is positioned in the rendering according to the one or more predefined locations.

In any of these embodiments, the system can be configured to receive the image data from an imaging system via a communication network.

In any of these embodiments, the system can be configured for transmitting the three-dimensional rendering to a clinical system via a communication network for display to a surgeon for preparing for the surgical procedure on the at least one region of the joint.

In any of these embodiments, the image data can include at least one of an MRI scan and a CT scan.

In any of these embodiments, the three-dimensional rendering can include a visual indication of the coordinate system.

In any of these embodiments, the coordinate system can include clock-face lines.

In any of these embodiments, the representation of the measurement can be provided adjacent to a clock-face line.

In any of these embodiments, the visual indication of the at least one region can include a heat map.

In any of these embodiments, the heat map can indicate an amount of tissue to remove to match the baseline anatomy.

In any of these embodiments, the joint can be a hip joint and the measurement of the characteristic can include at least one of an alpha angle and a lateral center edge angle.

In any of these embodiments, the joint can be a hip joint and the deviation from the baseline can be associated with at least one of a cam-type impingement and a pincer-type impingement.

In any of these embodiments, the three-dimensional rendering can include at least one indication of a location of a threshold characteristic value in the rendering.

In any of these embodiments, the at least one indication can include a curve connecting points that meet the threshold characteristic value.

In any of these embodiments, the joint can be a hip joint, the characteristic can be an alpha angle, and the threshold characteristic value can be 55 degrees, 65 degrees, or 75 degrees.

In any of these embodiments, the one or more programs can include instructions for displaying a spectrum bar graph that comprises the representation of the measurement of the characteristic of the joint, wherein regions of the spectrum bar graph are visually-coded to indicate normal and abnormal anatomical measurement ranges.

In any of these embodiments, the one or more programs can include instructions for displaying a coordinate system value that is associated with the representation of the measurement.

In any of these embodiments, the one or more programs can include instructions for displaying a representation of at least a portion of a resection tool and visually coding the representation to indicate a dimension of the at least a portion of the resection tool, wherein the visual coding is coordinated with the visual indication of the at least one region of the three-dimensional model that deviates from the baseline.

According to some embodiments, a non-transitory computer readable storage medium stores one or more programs, the one or more programs comprising instructions for execution by one or more processors for receiving image data associated with a joint of a subject; generating a three-dimensional model of at least a portion of the joint of the subject using the image data; identifying at least one region of the joint that deviates from a baseline anatomy by comparing at least a portion of the three-dimensional model to a baseline model; generating a measurement of a characteristic of the joint at one or more predefined locations using the three-dimensional model and a coordinate system; and generating a three-dimensional rendering of the model, wherein the three-dimensional rendering comprises: a visual indication of the at least one region of the three-dimensional model that deviates from the baseline, wherein the at least one region is visually indicated according to degree of deviation, and a representation of the measurement of the characteristic of the joint that is positioned in the rendering according to the one or more predefined locations.

According to some embodiments, a method for visualizing at least one region of a joint that deviates from a baseline anatomy for a surgical procedure on the at least one region of the joint includes receiving image data associated with a joint of a subject; generating a three-dimensional model of at least a portion of the joint of the subject using the image data; identifying at least one region of the joint that deviates from the baseline anatomy by comparing at least a portion of the three-dimensional model to a baseline model; generating a measurement of a characteristic of the joint at one or more predefined locations using the three-dimensional model and a coordinate system; and generating a three-dimensional rendering of the model, wherein the three-dimensional rendering comprises: a visual indication of the at least one region of the three-dimensional model that deviates from the baseline, wherein the at least one region is visually indicated according to degree of deviation, and a boundary line indicating a boundary within which the baseline anatomy lies.

In any of these embodiments, the boundary line can indicate a boundary within which a defined percentage of a reference population lies.

In any of these embodiments, the three-dimensional rendering of the model can include two boundary lines indicating boundaries within which a defined percentage of a reference population lies.

In any of these embodiments, the image data can include at least one of an MM scan and a CT scan.

In any of these embodiments, the three-dimensional rendering can include a visual indication of the coordinate system.

In any of these embodiments, the coordinate system can include clock-face lines.

In any of these embodiments, the visual indication of the at least one region can be a heat map.

In any of these embodiments, the heat map can indicate an amount of tissue to remove to match the baseline anatomy.

In any of these embodiments, the joint can be a hip joint and the deviation from the baseline can be associated with at least one of a cam-type impingement and a pincer-type impingement.

In any of these embodiments, the three-dimensional rendering can include at least one indication of a location of a threshold characteristic value in the rendering.

In any of these embodiments, the at least one indication can include a curve connecting points that meet the threshold characteristic value.

In any of these embodiments, the joint can be a hip joint, the characteristic can be an alpha angle, and the threshold characteristic value can be 55 degrees, 65 degrees, or 75 degrees.

In any of these embodiments, the method may further include displaying a spectrum bar graph that comprises a representation of a measurement of a characteristic of the joint, wherein regions of the spectrum bar graph are visually-coded to indicate normal and abnormal anatomical measurement ranges.

In any of these embodiments, the method may further include displaying a coordinate system value that is associated with the representation of the measurement.

In any of these embodiments, the method may further include displaying a representation of at least a portion of a resection tool and visually coding the representation to indicate a dimension of the at least a portion of the resection tool, wherein the visual coding is coordinated with the visual indication of the at least one region of the three-dimensional model that deviates from the baseline.

According to some embodiments, a system for generating a visualization of at least one region of a joint that deviates from a baseline anatomy for a surgical procedure on the at least one region of the joint, the system comprising one or more processors, memory, and one or more programs, wherein the one or more programs are stored in the memory and configured to be executed by the one or more processors, the one or more programs including instructions for: receiving image data associated with a joint of a subject; generating a three-dimensional model of at least a portion of the joint of the subject using the image data; identifying at least one region of the joint that deviates from the baseline anatomy by comparing at least a portion of the three-dimensional model to a baseline model; generating a measurement of a characteristic of the joint at one or more predefined locations using the three-dimensional model and a coordinate system; and generating a three-dimensional rendering of the model, wherein the three-dimensional rendering comprises: a visual indication of the at least one region of the three-dimensional model that deviates from the baseline, wherein the at least one region is visually indicated according to degree of deviation, and a boundary line indicating a boundary within which the baseline anatomy lies.

In any of these embodiments, the boundary line can indicate a boundary within which a defined percentage of a reference population lies.

In any of these embodiments, the three-dimensional rendering of the model can include two boundary lines indicating boundaries within which a defined percentage of a reference population lies.

In any of these embodiments, the system can be configured to receive the image data from an imaging system via a communication network.

In any of these embodiments, the system can be configured for transmitting the three-dimensional rendering to a clinical system via a communication network for display to a surgeon for preparing for the surgical procedure on the at least one region of the joint.

In any of these embodiments, the image data can include at least one of an MM scan and a CT scan.

In any of these embodiments, the three-dimensional rendering can include a visual indication of the coordinate system.

In any of these embodiments, the coordinate system can include clock-face lines.

In any of these embodiments, the visual indication of the at least one region can include a heat map.

In any of these embodiments, the heat map can indicate an amount of tissue to remove to match the baseline anatomy.

In any of these embodiments, the joint can be a hip joint and the deviation from the baseline can be associated with at least one of a cam-type impingement and a pincer-type impingement.

In any of these embodiments, the three-dimensional rendering can include at least one indication of a location of a threshold characteristic value in the rendering.

In any of these embodiments, the at least one indication can include a curve connecting points that meet the threshold characteristic value.

In any of these embodiments, the joint can be a hip joint, the characteristic can be an alpha angle, and the threshold characteristic value can be 55 degrees, 65 degrees, or 75 degrees.

In any of these embodiments, the one or more programs can include instructions for displaying a spectrum bar graph that comprises a representation of a measurement of a characteristic of the joint, wherein regions of the spectrum bar graph are visually-coded to indicate normal and abnormal anatomical measurement ranges.

In any of these embodiments, the one or more programs can include instructions for displaying a coordinate system value that is associated with the representation of the measurement.

In any of these embodiments, the one or more programs can include instructions for displaying a representation of at least a portion of a resection tool and visually coding the representation to indicate a dimension of the at least a portion of the resection tool, wherein the visual coding is coordinated with the visual indication of the at least one region of the three-dimensional model that deviates from the baseline.

According to some embodiments, a non-transitory computer readable storage medium stores one or more programs, the one or more programs comprising instructions for execution by one or more processors for: receiving image data associated with a joint of a subject; generating a three-dimensional model of at least a portion of the joint of the subject using the image data; identifying at least one region of the joint that deviates from a baseline anatomy by comparing at least a portion of the three-dimensional model to a baseline model; generating a measurement of a characteristic of the joint at one or more predefined locations using the three-dimensional model and a coordinate system; and generating a three-dimensional rendering of the model, wherein the three-dimensional rendering comprises: a visual indication of the at least one region of the three-dimensional model that deviates from the baseline, wherein the at least one region is visually indicated according to degree of deviation, and a boundary line indicating a boundary within which the baseline anatomy lies.

BRIEF DESCRIPTION OF THE DRAWINGS

Features will become apparent to those of ordinary skill in the art by describing in detail exemplary embodiments with reference to the attached drawings in which:

FIGS. 1A-1D are schematic views showing the range of motion of, for example, a hip joint;

DETAILED DESCRIPTION OF EXEMPLARY EMBODIMENTS

Figure 2:
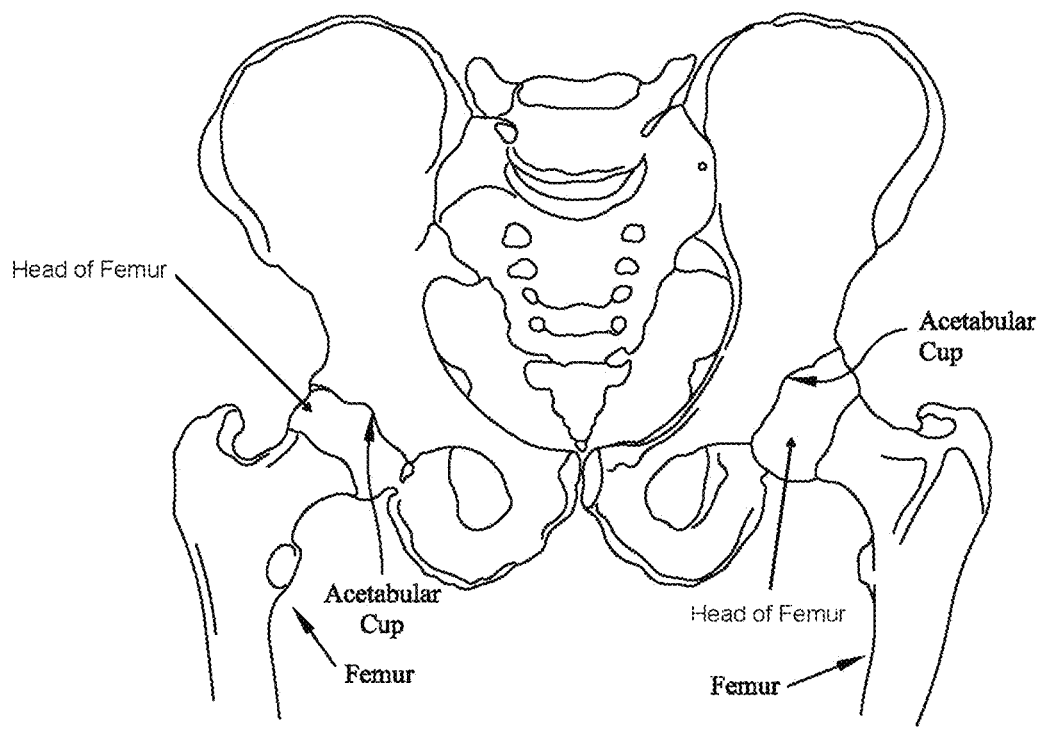
FIG. 2 is a schematic view showing the bony anatomy in the region of the hip joint.
Figure 3:
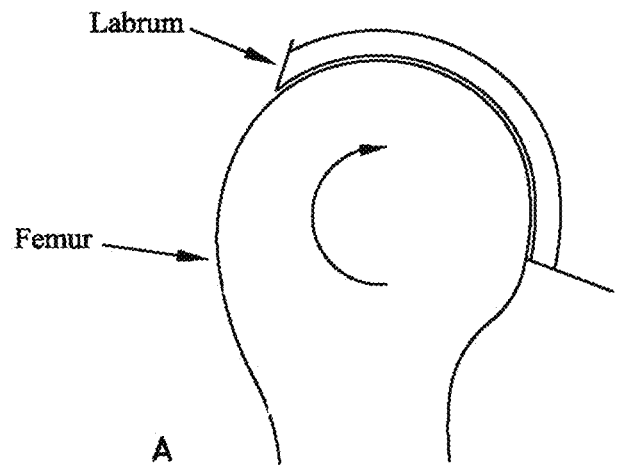
FIG. 3 is a schematic view showing cam-type FAI.
Figure 3:
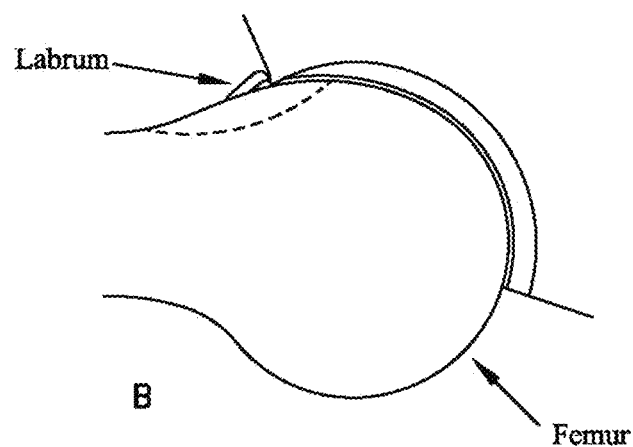
Figure 4:
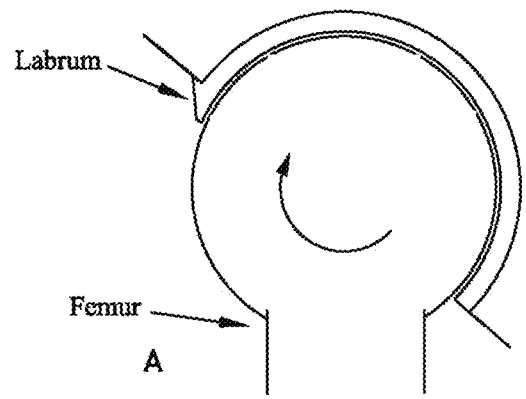
FIG. 4 is a schematic view showing pincer-type FAI.
Figure 4:
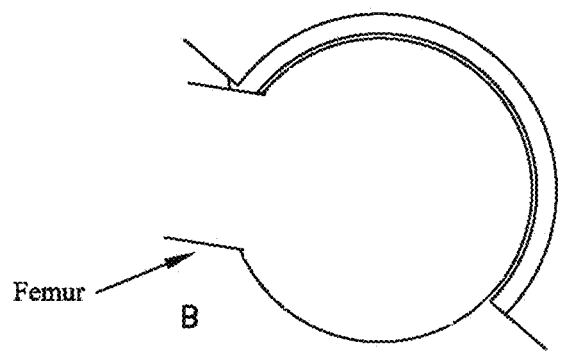
Figure 5:
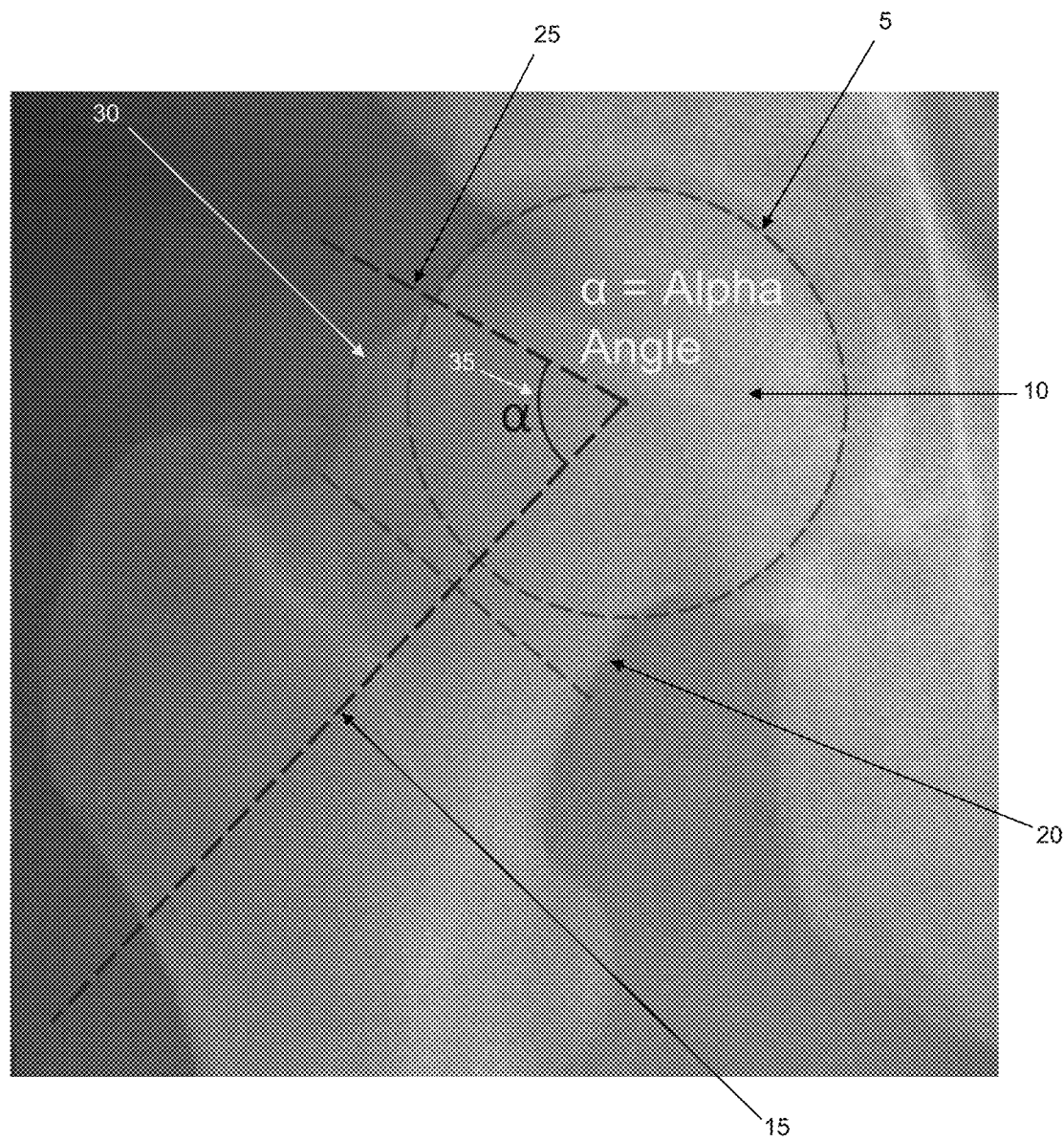
FIG. 5 is a schematic view showing how an Alpha Angle measurement is computed.
Figure 6:
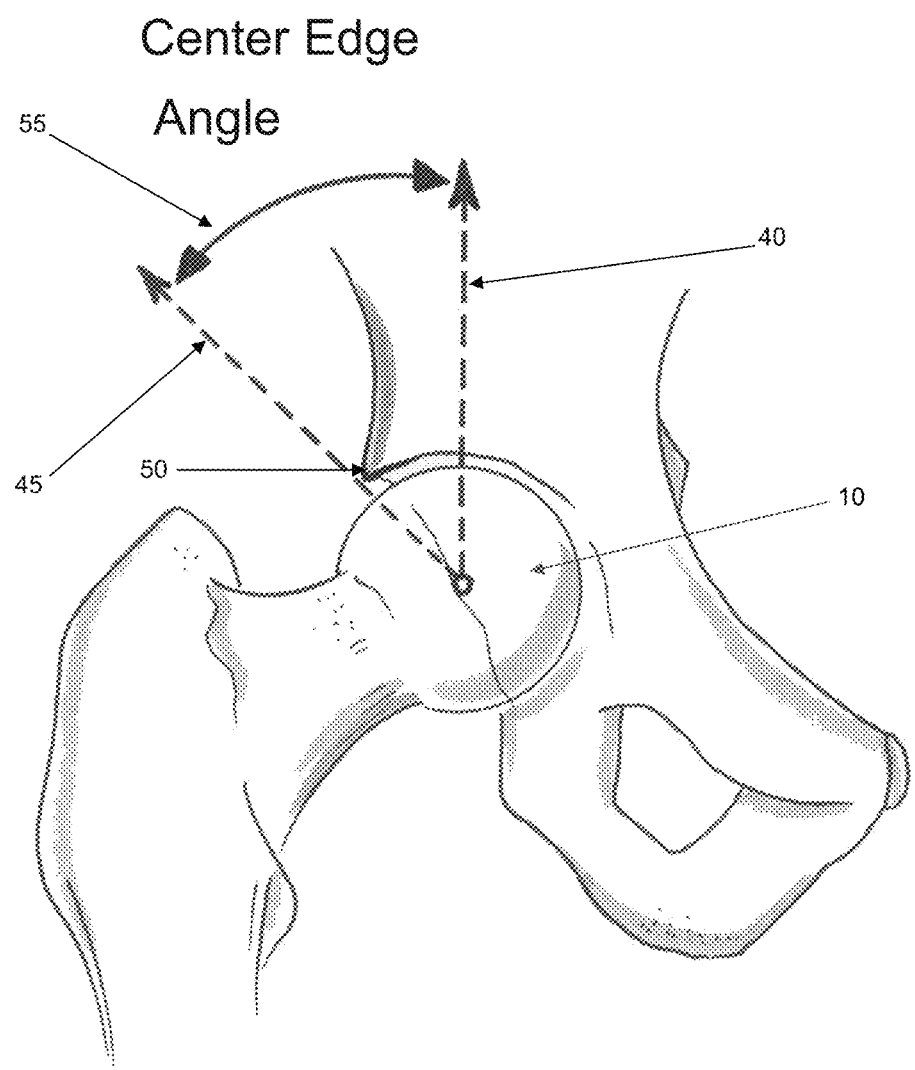
FIG. 6 is a schematic view showing how a Lateral Center Edge Angle measurement is computed.
Figure 7:
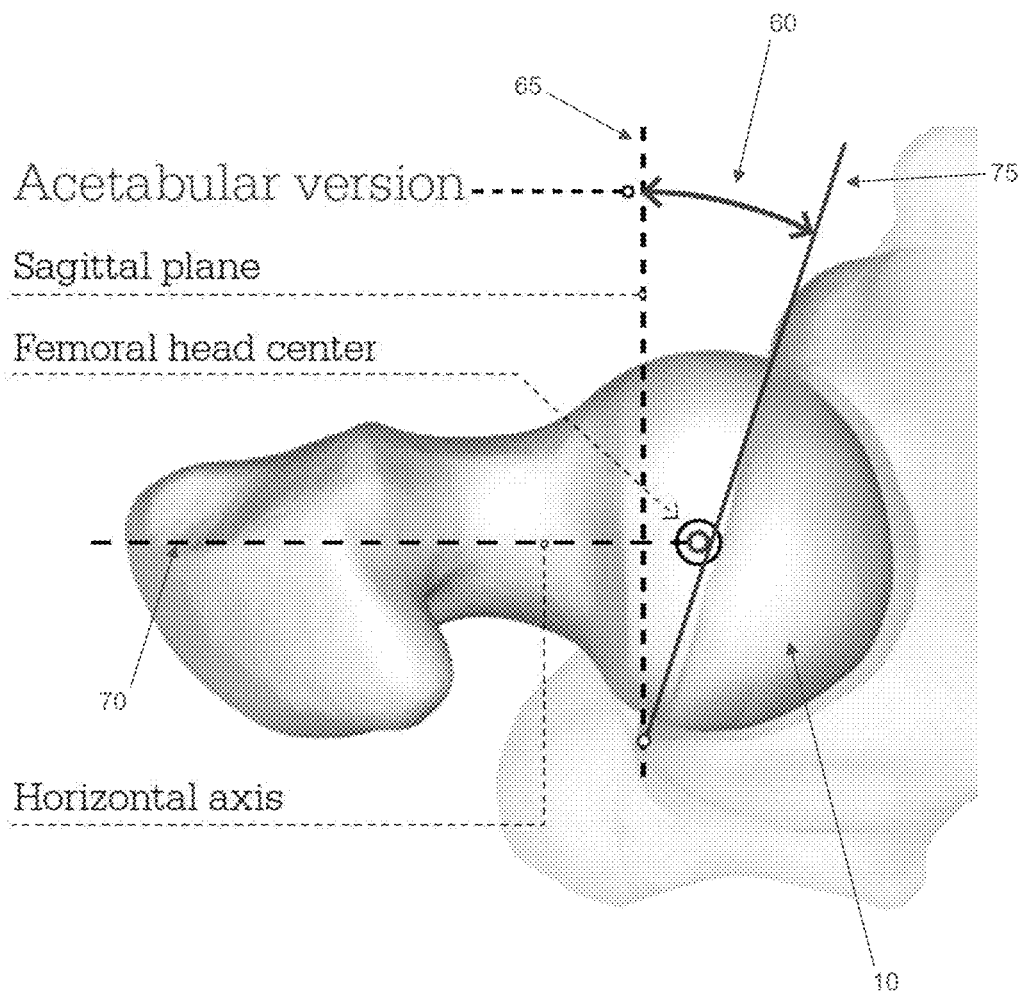
FIG. 7 is a schematic view showing how an Acetabular Version measurement is computed.
Figure 8:
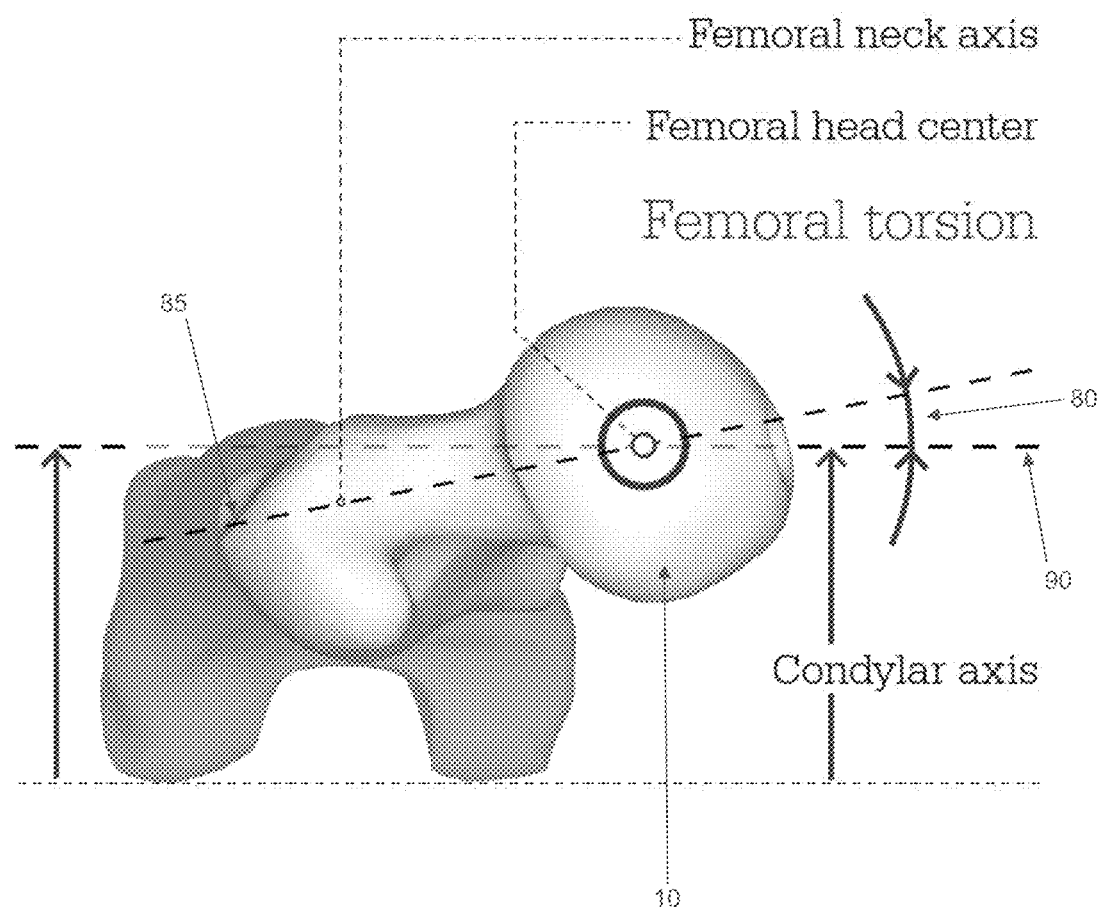
FIG. 8 is a schematic view showing how a Femoral Torsion measurement is computed.

Reference will now be made in detail to implementations and embodiments of various aspects and variations of the invention, examples of which are illustrated in the accompanying drawings. Various devices, systems, and methods are described herein. Although at least two variations of the devices, systems, and methods are described, other variations may include aspects of the devices, systems, and methods described herein combined in any suitable manner having combinations of all or some of the aspects described. Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

According to some embodiments, systems and methods according to the principles described herein can provide visualizations of at least one region of a joint that deviates from a baseline, which can assist a practitioner in planning for a surgical procedure on the at least one region of the joint. For example, a visualization of a hip joint of a subject can be provided that indicates a location of a hip joint pathology (e.g., a condition or a disorder), such as an FAI, and an amount of bone that may be removed to match a baseline anatomy.

Visualizations can be generated from a three-dimensional model of the joint of a subject that is generated from one or more scans of the subject. Information regarding deviations from a baseline anatomy can be generated by comparing the three-dimensional model to baseline data. The baseline data can represent target joint morphology. Target joint morphology can be any joint morphology that may be desired for a given subject. Target joint morphology can be based on the anatomy representative of any reference patient population, such as a normal patient population. For example, baseline data can be a model of a "normal" joint that is derived from studies of a healthy patient population and/or from a model generated based on measurements, computer simulations, calculations, etc. The terms target, baseline, and reference are used interchangeably herein to describe joint morphology characteristics against which a subject's joint morphology is compared.

The three-dimensional model and the information regarding deviations from a baseline/target anatomy can be used to generate a three-dimensional rendering of the joint that shows the deviations from the baseline/target anatomy. Visualizations can be created that include the three-dimensional rendering and/or other information related to the subject joint.

Although the following examples often refer to hip joints, hip joint pathologies, and hip joint characteristics and measurements, it is to be understood that systems, methods, techniques, visualizations, etc., for analyzing and visualizing other joints, including knee joints, shoulder joints, elbow joints, etc., are within the scope of the invention.

According to some embodiments, a physician can be provided with improved guidance with respect to the extent of a deviation of a joint morphology from a target morphology, and how much bone should be removed to achieve the target morphology, for example, during a minimally-invasive arthroscopic procedure or open surgical procedure. According to some embodiments, visualizations can provide a physician with improved guidance with respect to morphology measurements for a hip joint, including the Alpha Angle, Lateral Center Edge Angle, Acetabular Version and Femoral Torsion, Tönnis angle, neck shaft angle, and acetabular coverage that can help a practitioner gauge a deviation of the subject morphology from a target morphology.

FIGS. 9a-d illustrate various pre-operative planning visualization features, according to some embodiments. According to various embodiments, any of the various features illustrated in FIGS. 9a-d may be generated individually and/or in combination with any of the other features illustrated in FIGS. 9a-d. It should be appreciated that, any of the information, visualizations, features, data, measurements, etc., illustrated in FIGS. 9a-d may be provided to a user in any form. For example, one or more features may be provided in one or more user interfaces of a web page, an "app" for a tablet or smartphone or computer, etc.

"Clock-face lines" 2 are artificial virtual objects inserted into the patient-specific virtual 3D model rendered from scan data. The use of clock-face lines are as described in the literature, and are useful for identifying positions within the hip joint.

Resection depth ("pincer/cam depth") 3 is the distance between the patient's actual bone surface and the target bone surface, where the target bone surface is defined by the literature available on a particular measure of hip morphology (e.g., such as literature describing the results of a study of a large sample of patients having "normal" anatomy).

The FAI lesion 4 (in the case of the lesion identified by this visualization, a pincer-type FAI lesion) is color-coded according to resection depth.

The cross-sectional view of a bur tool 5 (used to resect the bone) is color-coded in order to relate it dimensionally to various resection depths. The cross-sectional view of a bur was chosen because it is the instrument which is typically used in arthroscopic surgery to remove bone pathologies. The use of a cross-sectional view of a bur helps to tie together the pre-operative planning to the intra-operative work by providing an approximate guide for the depth of bone recommended to be removed by the report relative to the dimensions of the tool. However, other shapes or sizes of surgical instruments could be used in place of the cross-sectional view of a bur. For instance, the report could be configured to show the resection depth on a smaller or larger bur, or on a cross-sectional view of a different bur, or a chisel or bone rasp depending on the physician's own preferences.

The outer arcuate line 6 identified by this footnote illustrates the position of an acetabular rim boundary within which 95% of a normal hip population will lie. A patient with a bone surface which lies outside (laterally) of this line is considered to have pincer-type FAI for the purposes of the report.

The inner arcuate line 7 identified by this footnote illustrates the position of an acetabular rim boundary outside of which 95% of a normal hip population will lie. A patient with a bone surface which lies outside (medially) of this line may be considered to have an unstable hip joint.

Graphic 8 illustrates the patient-specific measurement of the Acetabular Version at the "3 o'clock" position, shown (for example) with a marker labelled "28°". The marker is based upon the specific measure of Acetabular Version made for the patient and is positioned along a spectrum labelled with representative Acetabular Version angles of 0°, 15°, 20° and 25°, and where the angle spectrum is color-coded to show population distributions (green is "normal", red is "abnormal" and yellow is "marginal" or "borderline"), although other colors could be used for these representations of the anatomy, as could additional colors for more resolution in the different categories of pathologic variations.

Table 9 illustrates how a particular measure (i.e., the Later Center Edge Angle) changes with increasing degrees of resection depth (at the "12 o'clock" position), as if the virtual 3D model were modulated to reflect increasing degrees of bone resection. The specific changes in the Center Edge Angle with increasing degrees of bone resection may help the physician evaluate how much bone can/should be resected on the acetabular rim.

Graphic 10 is displayed if one of the measurements determined by the pre-operative planning tool is considered to be abnormal (e.g., in the red range) and representative of hip instability. If none of the measurements indicates instability, the graphic is not shown. This feature helps the physician decide if the acetabular resection should be conservative (i.e., if less bone should be removed) and in cases of severe hip instability whether additional treatment such as a peri-acetabular osteotomy may be appropriate.

Graphic 11 illustrates patient-specific measurements of the Alpha Angle at specific clock-face positions; note that the patient-specific measurements of the Alpha Angle are superimposed on an image rendered from the virtual 3D model and are not artificial virtual objects inserted into the virtual 3D model.

The FAI lesion 12 (in the case of the lesion identified by this visualization, a cam-type FAI lesion) is color-coded according to the desired (i.e., target) resection depth, wherein the desired resection depth is the distance between the patient's actual bone surface and a target bone surface. According to some embodiments, the target bone surface can established by what is defined as normal anatomy, such as from studies published in the literature. In some embodiments, the target bone surface can be generated primarily using the assumption that a femoral head is spherical and from Alpha Angle measurements.

The "12 o'clock" and "9 o'clock" clock-face lines, and the "annular Alpha Angle of 55° line" (collectively indicated by reference numeral 13) may be artificial virtual objects inserted into a virtual 3D model. In other embodiments, this information is not inserted into the virtual 2D model, but instead are rendered on the 3D rendering generated from the virtual 3D model. In some embodiments, other information, such as the remaining clock-face and Alpha Angle lines are rendered on the 3D rendering generated from the virtual 3D model.

Figure 9A:
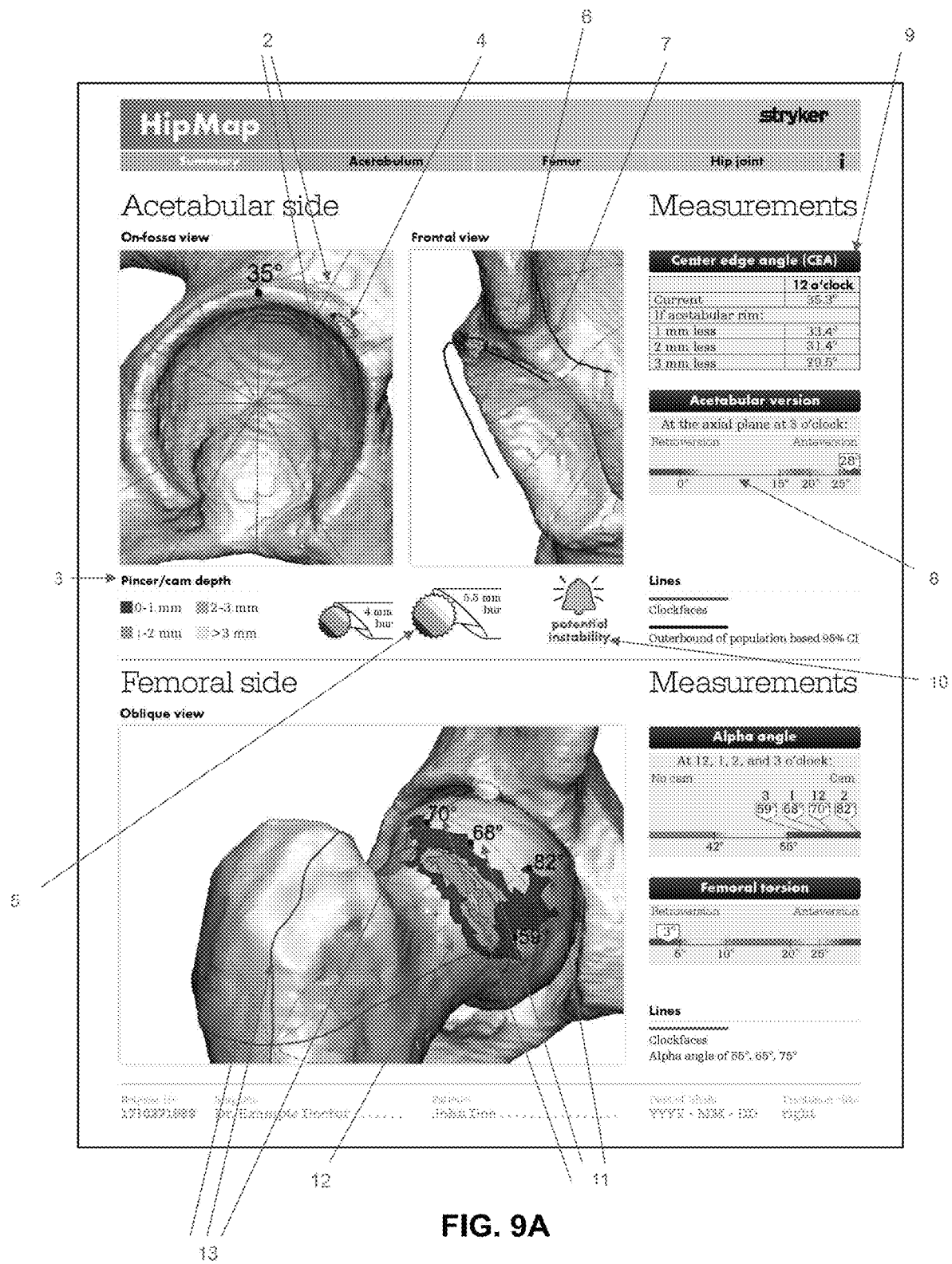
FIGS. 9A-9D illustrate various pre-operative planning visualizations, according to some embodiments.
Figure 9B:
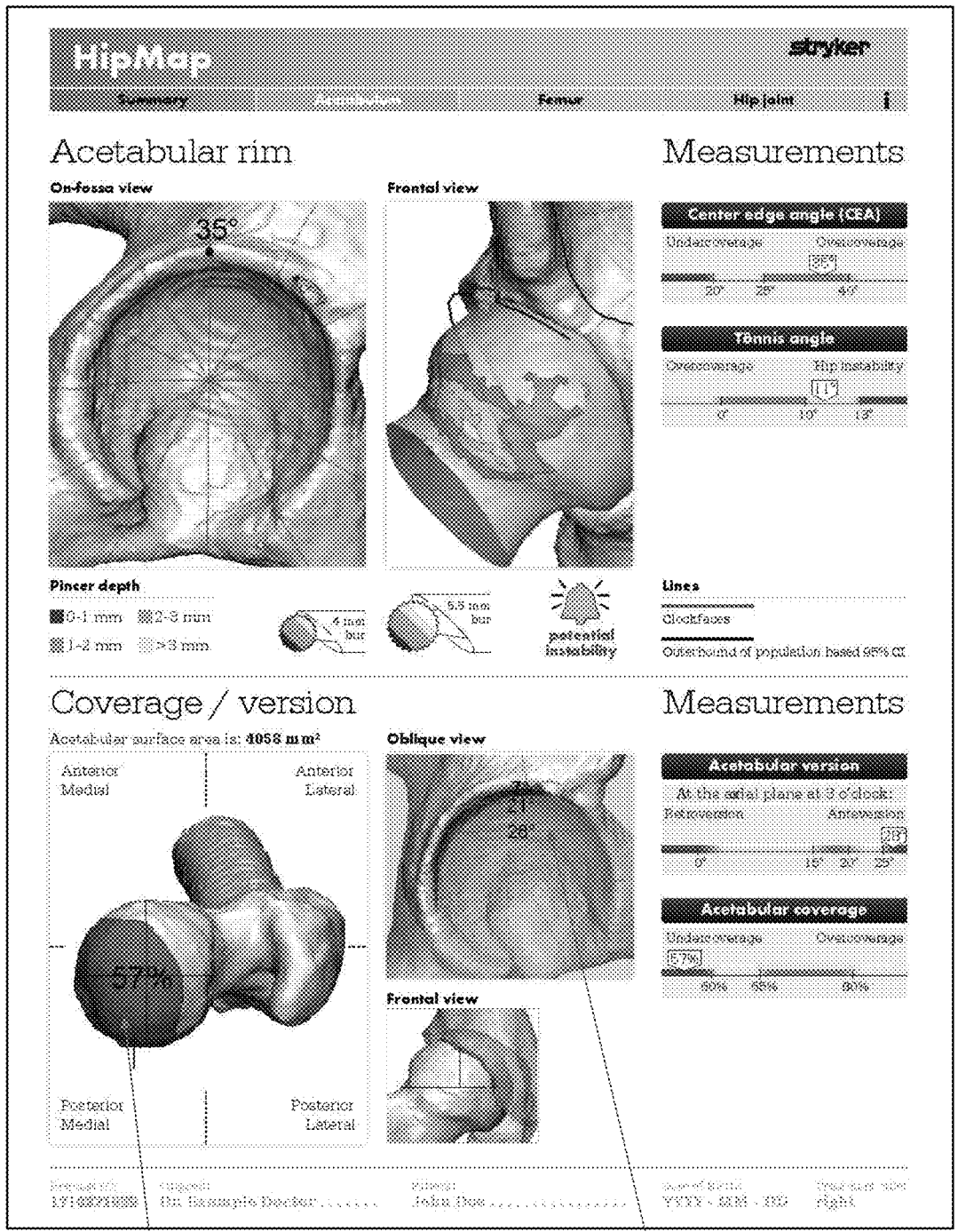

The shaded region 14 in FIG. 9*b* represents the superior portion of the femoral head which is covered by the projected area of the acetabulum when the femur is in a neutral position with respect to the acetabulum (while the patient is standing or laying down). The quadrants indicate the medial/lateral and posterior/anterior portions of the femoral head.

The horizontal lines 15 indicate the Acetabular Version at the "3 o'clock", "2 o'clock" and "12 o'clock" positions of the acetabulum. The sagittal plane at the center of the femoral head is shown transparently for graphical reference and supports an inference of the orientation of the acetabular socket at the other clock-face positions.

Figure 9C:
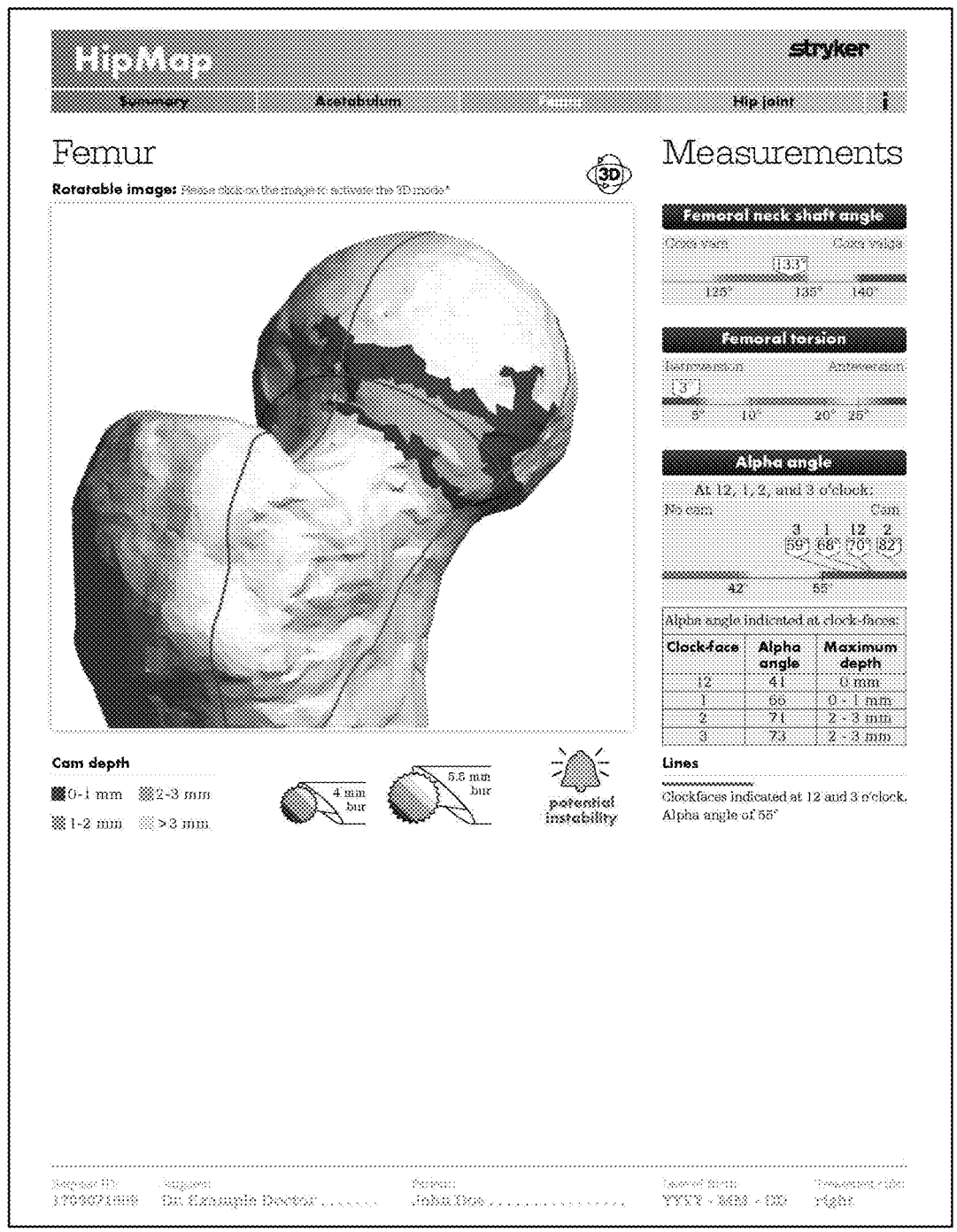

FIG. 9*c* illustrates a rotatable 3D rendering that may be provided to enable a practitioner to rotate the 3D rendering on a display screen (e.g., using a user input device such as a touch screen, mouse, keyboard, voice control interface, etc.).

Figure 9D:
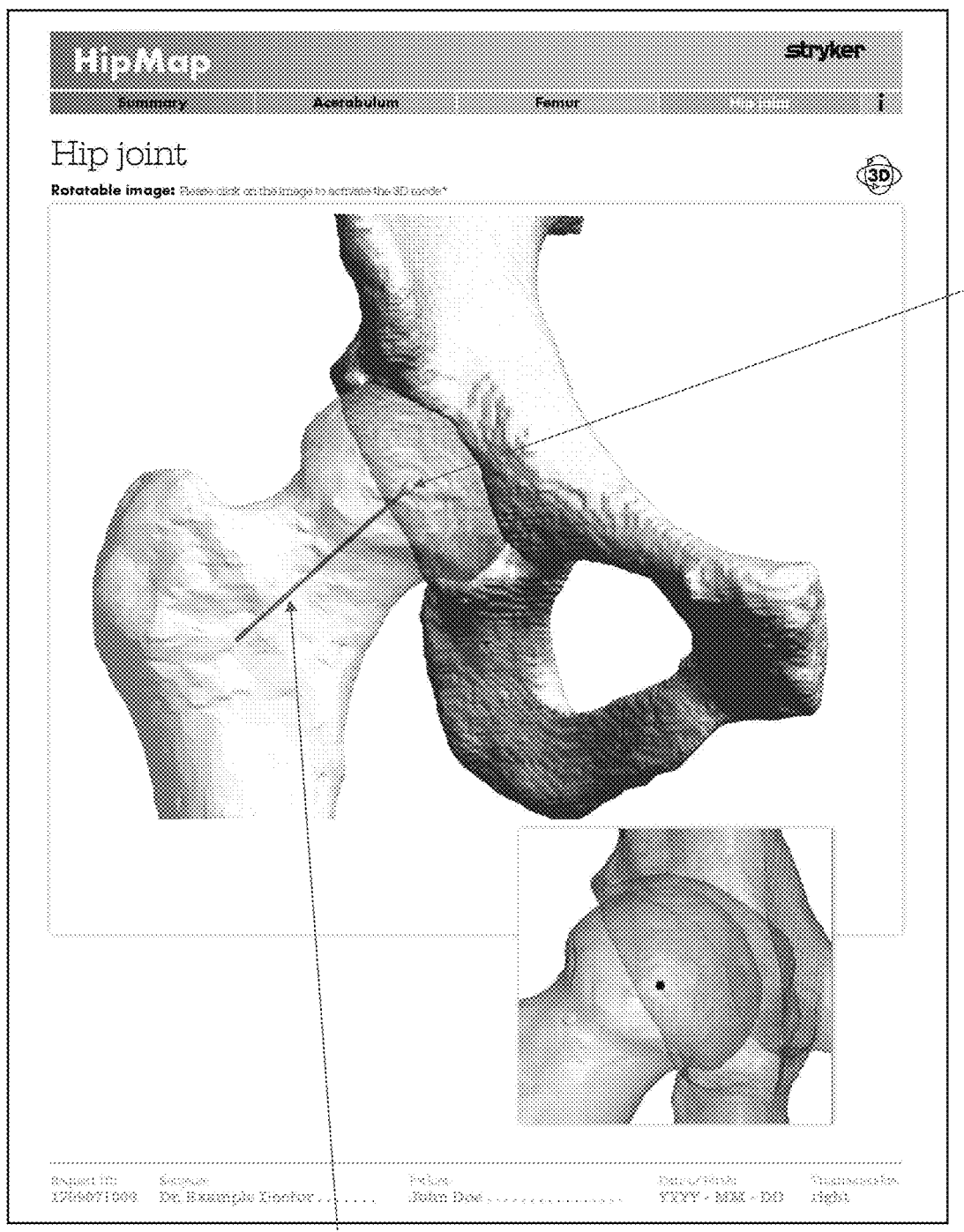

In FIG. 9*d*, the center 16 of the femoral head is represented by a spherical virtual object which is inserted into the virtual 3D rendering. The center of the femoral neck 17 is represented by a virtual rod which is inserted into the virtual 3D rendering. The virtual 3D rendering may be rotatable.

Figure 10:
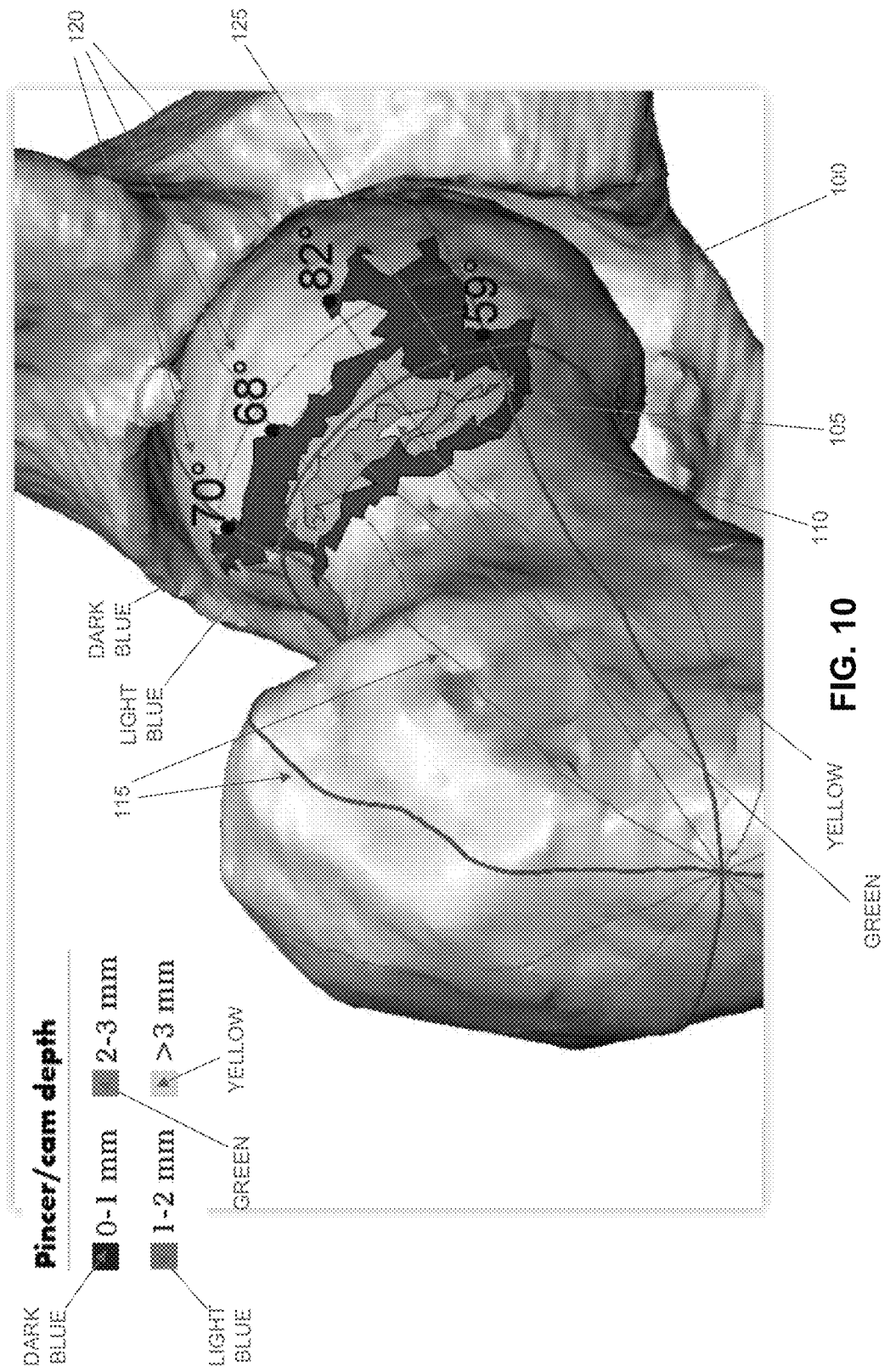
FIGS. 10 and 11 illustrate exemplary 3D renderings having clock-face line(s) and visually-coded pathology regions and pathology measurement information, according to some embodiments.
Figure 11:
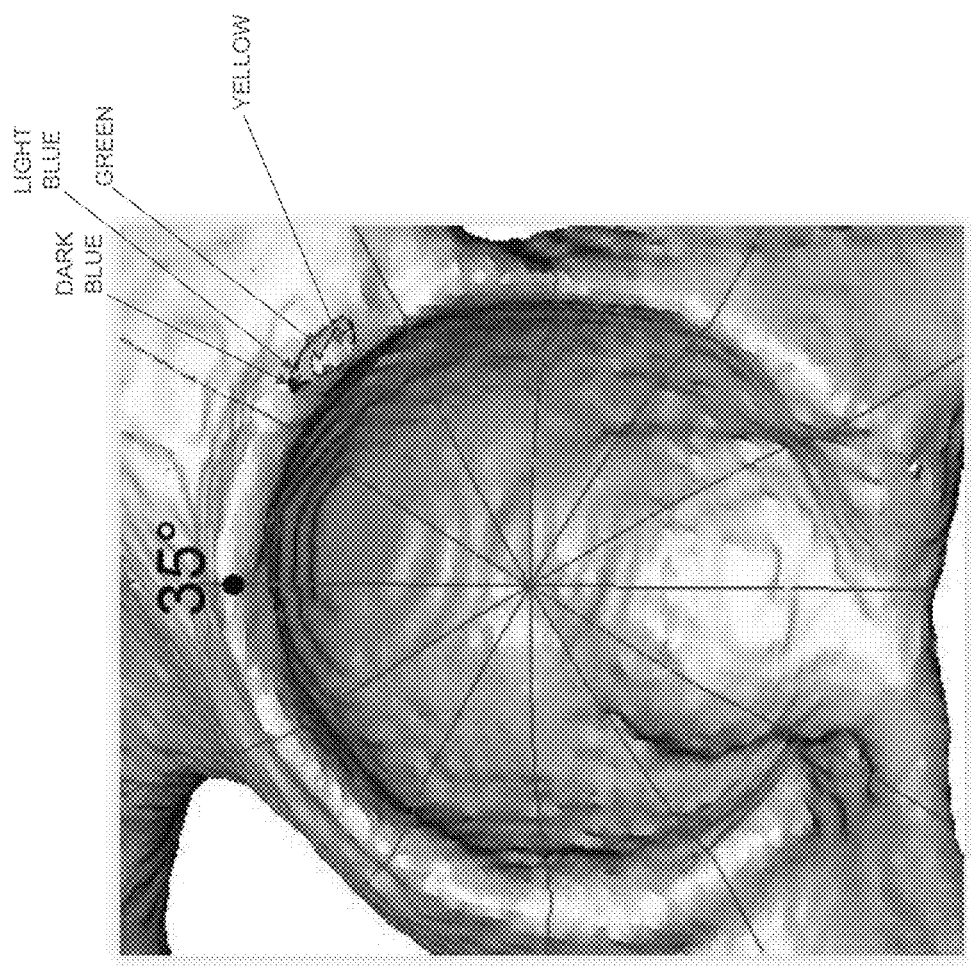

FIGS. 10 and 11 (FIG. 10 relating to cam-type FAI and FIG. 11 relating to pincer-type FAI) illustrate visualizations that include a unique combination of elements not previously provided in a single image. More particularly, these displays provide information about a pathology (e.g., a lesion, a bony deformity, or another condition) of a hip joint by providing a three-dimensional rendering 100 of at least a portion of a hip joint which contains: (i) a region 105 associated with a pathology, with the region 105 being visually-coded 110 on the three-dimensional rendering 100 so as to indicate the height (or thickness or depth or dimension) of the region 105 relative to a target anatomy; (ii) clock-face lines 115; and (iii) a representation of the measurement 120 of a characteristic of the joint that is positioned at clock-face positions. The measurement may relate to an extent of a pathology.

Clock-face lines 115 are of the sort which are well known in the art, and which are widely used for identifying positions within the hip joint (e.g., for identifying rotational positions about the femoral head, the acetabular cup, etc.).

In one preferred form of the invention, the measurement 120 for a particular clock-face position is positioned adjacent to the region 105 and adjacent to the clock-face line 115 pertaining to the measurement.

As shown in FIG. 10, the pathology may be a cam lesion, and the measurement may comprise an Alpha Angle measurement. Furthermore, the three-dimensional rendering 100 of the at least a portion of the hip joint may be include at least one Alpha Angle arc 125 set at a pre-determined Alpha Angle position. By way of example but not limitation, the pre-determined Alpha Angle measurement may be selected from the group consisting of approximately 35, 45, 55, 65, 75, 85, and 95 degrees. The pre-determined Alpha Angle measurement may be selected from the group consisting of 5 degree and/or 10 degree increments. The pre-determined Alpha Angle measurement may be selected from the group consisting of both 5 degree and/or 10 degree increments and a group consisting of approximately 42 degrees and approximately 55 degrees.

As shown in FIG. 11, the pathology may be a pincer lesion, and the measurement may comprise a Center Edge Angle measurement.

In one preferred form of the invention, the region 105 is color-coded to indicate the height of the pathology relative to a target anatomy (e.g., non-pathologic, or desired, anatomy, which may be derived from measurements on subjects with normal bone morphology). Alternatively, the visual coding provided on the surface of the pathology may use non-color-coding, e.g., the visual coding may use varying shading, varying fill patterns, varying fill densities, etc.

Figure 13:
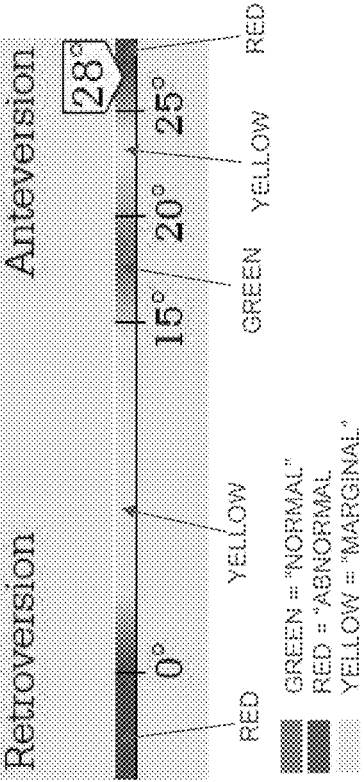
FIGS. 12-14 are schematic views illustrating spectrum bar graphs, according to some embodiments.
Figure 12:
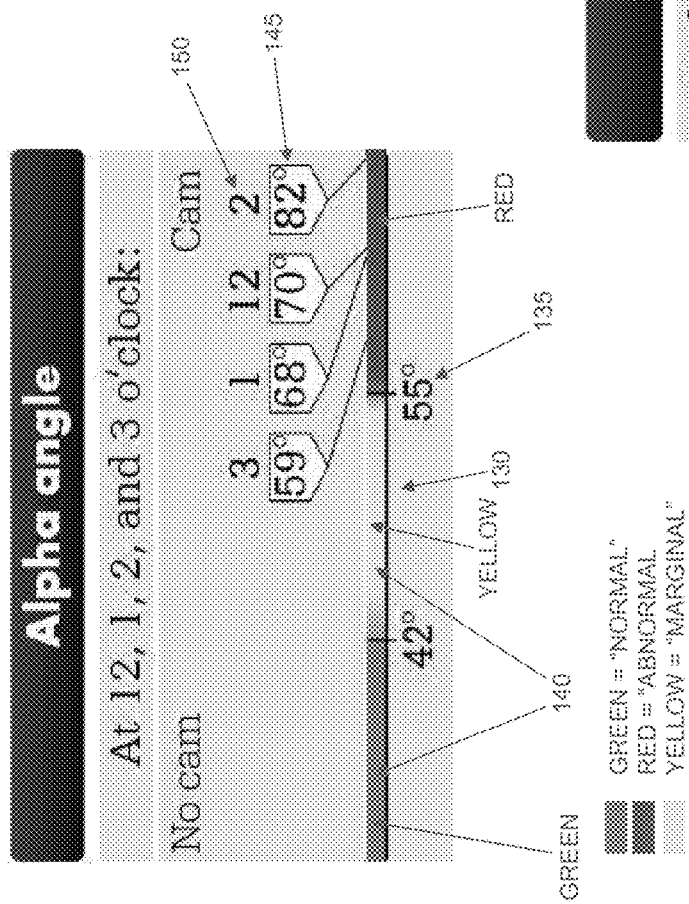
Figure 14:
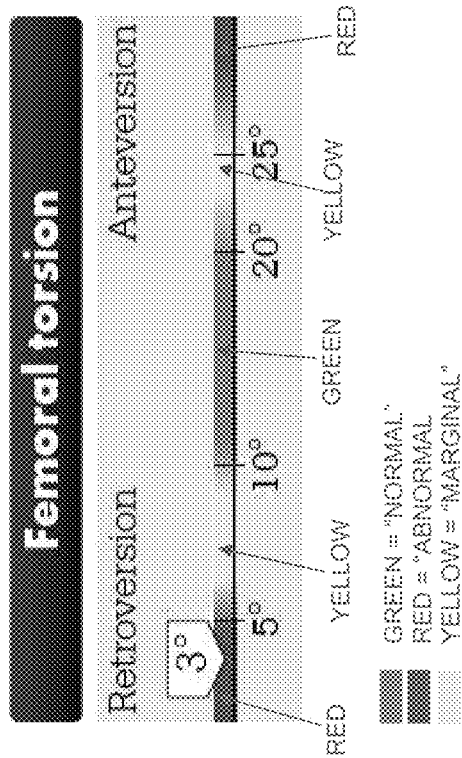

The visualizations shown in FIGS. 12-14 (FIG. 12 relating to Alpha Angle measurements, FIG. 13 relating to Acetabular Version measurements, and FIG. 14 relating to Femoral Torsion measurements) comprise a unique combination of elements not previously provided in a single image. More particularly, these displays provide information about an anatomical characteristic of a hip joint, by combining: (i) a spectrum bar graph 130, wherein anatomical measurement indicia 135 are disposed along the length of the spectrum bar graph 130, and further wherein regions of the spectrum bar graph 130 are visually-coded at 140 to indicate normal, abnormal and marginal (borderline) anatomical measurement ranges on the spectrum bar graph 130; and (ii) annotating the spectrum bar graph 130 with at least one anatomical measurement 145 associated with the hip joint, or an index combining several measures into one.

Note that the anatomical measurement indicia 135 may be disposed at regular intervals (e.g., 5 degree intervals) along spectrum bar graph 130, or the anatomical measurement indicia 135 may be at the border between two of the normal, abnormal and marginal (borderline) measurement ranges.

According to an embodiment, regions of the spectrum bar graph 130 are visually-coded to indicate normal, abnormal and marginal (borderline) anatomical measurement ranges on the spectrum bar graph 130.

As shown in FIG. 12, the anatomical characteristic may be a cam lesion, and the anatomical measurement information may comprise an Alpha Angle measurement. Furthermore, the spectrum bar graph may be annotated with clock-face indicia 150 relating to the location at which the anatomical measurement was determined.

The anatomical characteristic may be a pincer lesion, and the anatomical measurement information may comprise a Center Edge Angle measurement.

The anatomical characteristic may be Acetabular Version (FIG. 13) or Femoral Torsion (FIG. 14), and the anatomical measurement information may be a retroversion/anteversion angle measurement.

According to an embodiment, the regions of the spectrum bar graph 130 are color-coded to indicate normal, abnormal and marginal (borderline) anatomical measurement ranges on the spectrum bar graph 130. Alternatively, the visual coding provided on the regions of the spectrum bar graph 130 may use non-color-coding, e.g., the visual coding may use varying shading, varying fill patterns, varying fill densities, etc.

Figure 15:
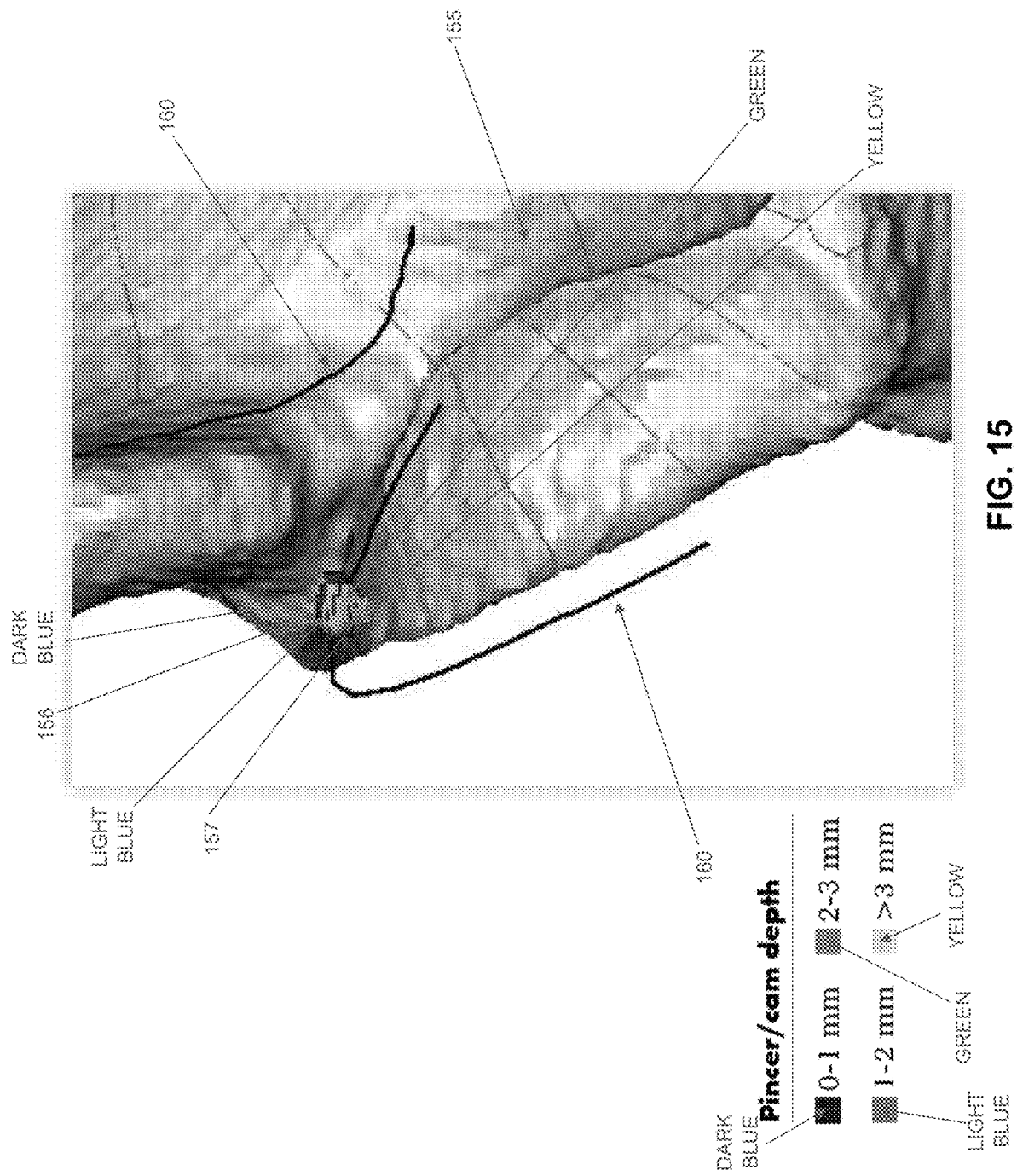
FIG. 15 is a schematic view illustrating a 3D rendering having acetabular rim ranges, according to some embodiments.

The visualization shown in FIG. 15 (relating to pincer-type FAI) comprises a unique combination of elements not previously provided in a single image. More particularly, this display provides information about the acetabular rim of a hip joint, by providing a 3D rendering 155 of at least a portion of the acetabular rim of a hip joint that includes: (i) a region 156 associated with a pathology, with the region 156 being visually-coded 157 on the three-dimensional rendering 155 so as to indicate the height (or thickness or depth or dimension) of the region 156 relative to a target anatomy; and (ii) an arcing boundary line 160 indicating an acetabular boundary within which the anatomy of at least 95% of a normal population lies.

If desired, clock-face lines may also be incorporated in the display.

According to an embodiment, the arcing boundary line 160 indicates an acetabular boundary within which the anatomy of at least 95% of a normal population lies.

The three-dimensional rendering 155 of at least a portion of the acetabular rim of the hip joint may be annotated with at least two arcing boundary lines 160 indicating acetabular boundaries within which the anatomy of at least 95% of a reference population lies.

In one preferred embodiments, the three-dimensional rendering 155 is generated by rendering an image of a user-rotatable three-dimensional model of at least a portion of the acetabular rim of a hip joint, and the arcing boundary line 160 is locked in position relative to the three-dimensional model of at least a portion of the acetabular rim of a hip joint. This may be achieved by forming the arcing boundary line 160 as a virtual object inserted into the three-dimensional model of at least a portion of the acetabular rim of a hip joint.

Figure 16:
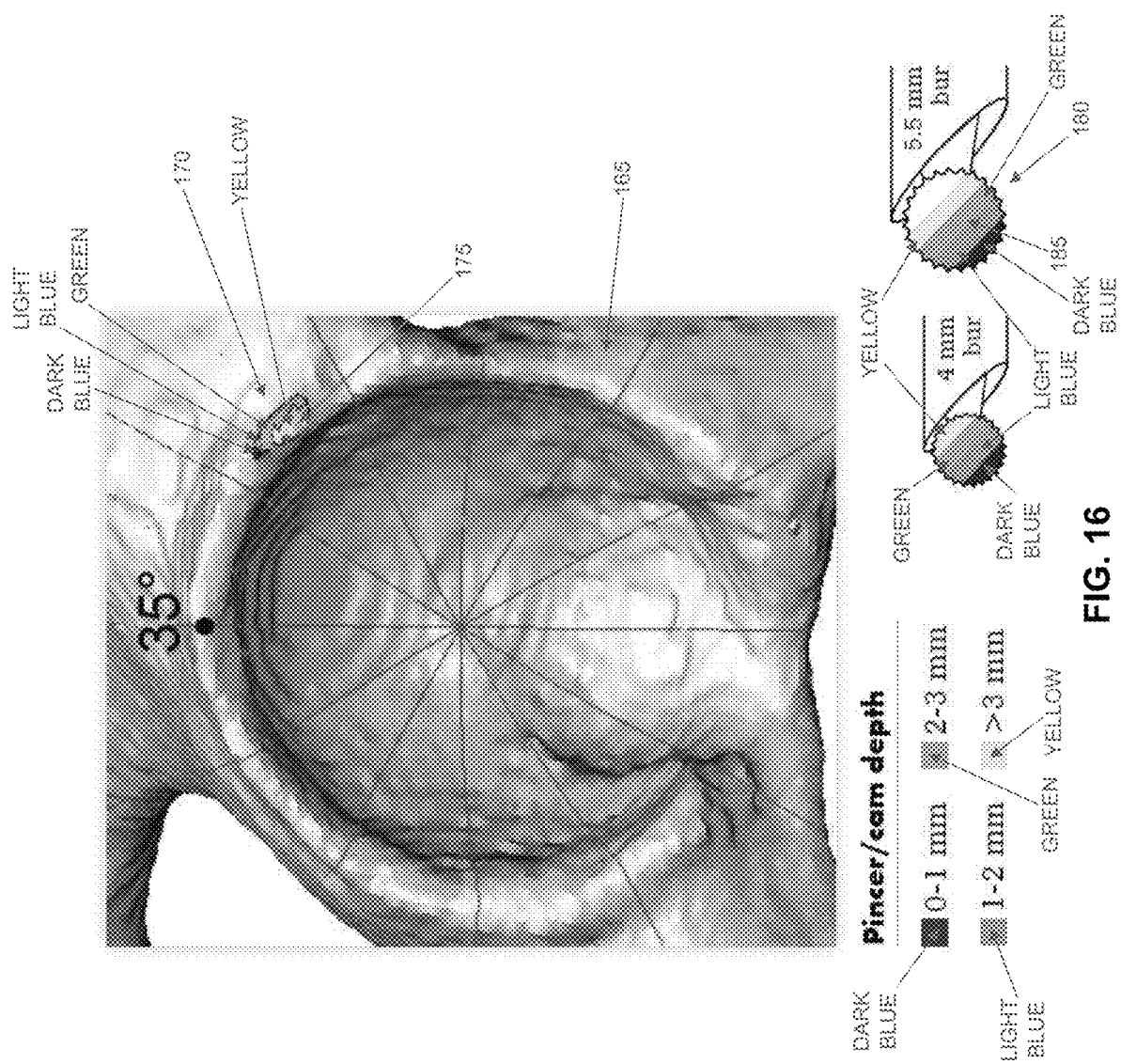
FIG. 16 is a schematic view illustrating a resection tool representation having color coding in combination with a 3D model and visually-coded pathology surfaces.

In FIG. 16, a visualization is provided that includes a unique combination of elements not previously provided in a single image. More particularly, this visualization provides information about resecting a bony deformity of a hip joint, by providing a three-dimensional rendering 165 of at least a portion of a hip joint which contains the bony deformity, with the region 170 of the bony deformity being visually-coded at 175 on the three-dimensional rendering 165 so as to indicate a dimension of the bony deformity taken relative to a target anatomy. The visualization may include a representation 180 of at least a portion of a tool for performing a resection of the bony deformity, wherein at least a portion of the tool is visually-coded at 185 so as to indicate a dimension of at least a portion of the tool, and further wherein the visual-coding at 185 of the dimension of at least a portion of the tool is coordinated with the visual-coding at 175 of the region 170 of the bony deformity taken relative to a target anatomy. Such coordination between the surgical tool and the images in the report provides the surgeon with a visual reference for dimensions, such as the depth of resection.

According to an embodiment, the region of the bony deformity is color-coded to indicate a dimension of the bony deformity taken relative to a desired anatomy, and the representation of the at least a portion of the tool is color-coded to indicate a dimension of the at least a portion of the tool. Alternatively, the visual coding provided on the surface of the bony deformity and the visual coding provided on the tool may use non-color-coding, e.g., the visual coding may use varying shading, varying fill patterns, varying fill densities, etc.

In some embodiments, the representation of at least a portion of the tool comprises a side view of the at least a portion of the tool, which may include at least the distal end of the tool.

Figure 17:
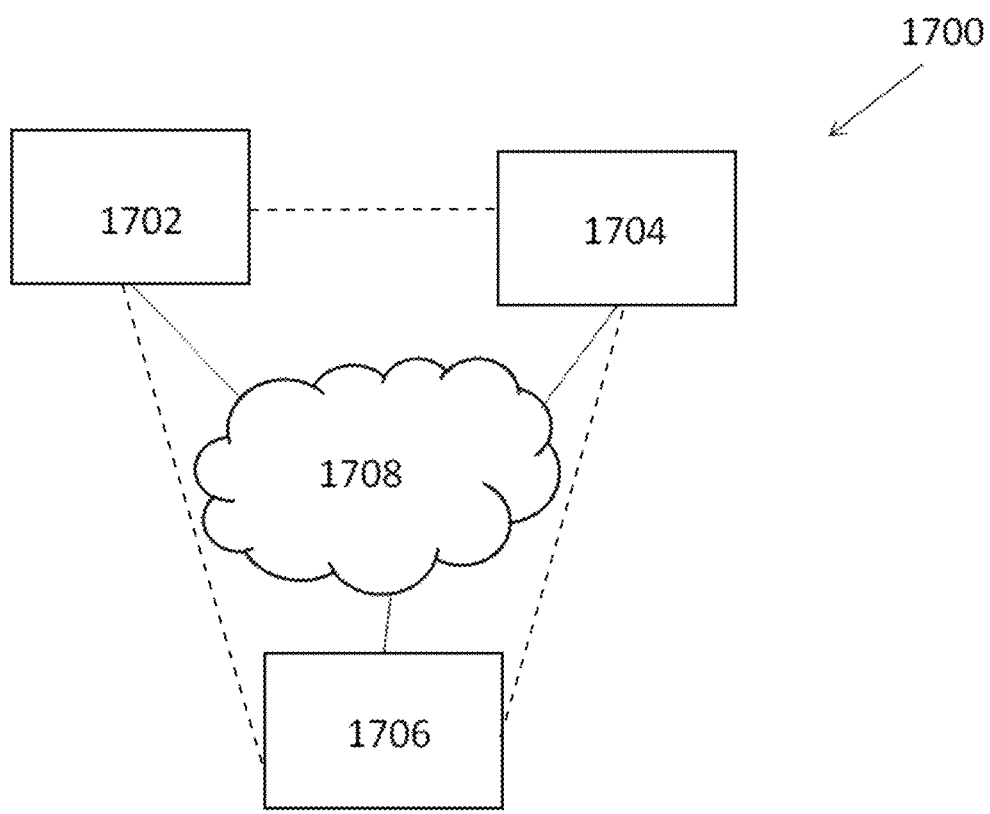
FIG. 17 illustrates a system for imaging a joint of a subject, generating 3D renderings of the joint, and displaying the 3D renderings to a practitioner, according to various embodiments.

FIG. 17 illustrates a system 1700 for imaging a joint of a subject, generating 3D renderings of the joint, and displaying the 3D renderings to a practitioner, according to various embodiments. System 1700 includes an imaging subsystem 1702 for imaging the joint of the subject, a visualization generating subsystem 1704 for generating visualizations of the joint from imaging generated by the imaging subsystem, and a display subsystem 1706 for displaying generated visualizations to a practitioner. The subsystems may be communicatively connected via a network 1708, such as a local area network, a wide area network, a combination of local and wide area networks, or any suitable communication network. In some embodiments, the subsystems may be directly connected to one another such that data is transferred from one subsystem to another directly, without being routed through a network. For example, an imaging subsystem and a visualization generating subsystem may be different portions of the same operating suite.

Imaging subsystem 1702 can include an imager for generating imaging data for a subject. Imaging data can include, for example, MRI scans, CT scans, x-rays, fluorescence imaging data, or any suitable imaging data for imaging a joint of a subject. In some embodiment, the imaging subsystem 1702 can include one or more imaging data processing systems for processing imaging data generated by an imager. The imaging subsystem 1702 can include one or more data storage systems for storing imaging data. The imaging subsystem 1702 can be configured to transmit imaging data for a joint of a subject to visualization generating subsystem 1704. For example, after an imaging session in which a joint of a subject was imaged, imaging data generated during the session can be transmitted to the visualization generating subsystem 1704 for generating visualizations, according to the principles described above. In some embodiments, data is transferred from an imaging subsystem to a visualization generating subsystem 1704 in the same facility, such as a central computing system. In other embodiments, data is transferred to a remote system, such as one operated by a third party that provides a visualization generation service.

The visualization generating subsystem 1704 can be configured to receive imaging data and use some or all of the imaging data for generating a three-dimensional model of at least a portion of the joint of the subject. The subsystem 1704 can identify at least one region of the joint that deviates from a baseline anatomy by comparing at least a portion of the three-dimensional model to a baseline model. The subsystem 1704 can generate a measurement of a characteristic of the joint at one or more predefined locations using the three-dimensional model and a coordinate system; and can generate a three-dimensional rendering of the model, according to the principles described herein. The three-dimensional rendering can include a visual indication of the at least one region of the three-dimensional model that deviates from the baseline, wherein the at least one region is visually indicated according to degree of deviation. The three-dimensional rendering can be a component of a visualization that includes any other relevant information as described herein.

The visualization generating subsystem 1704 can be configured to transmit visualizations, such as those including three-dimensional renderings, to display subsystem 1706 for displaying the generated visualizations to a practitioner to help the practitioner plan a surgical procedure to correct a pathology analyzed and indicated in the visualization. For example, the visualizations can be displayed to a computer used by a practitioner via, for example, a web interface or an app. The display subsystem can include one or more operating room displays for displaying the visualizations to the practitioner during surgery.

Figure 18:
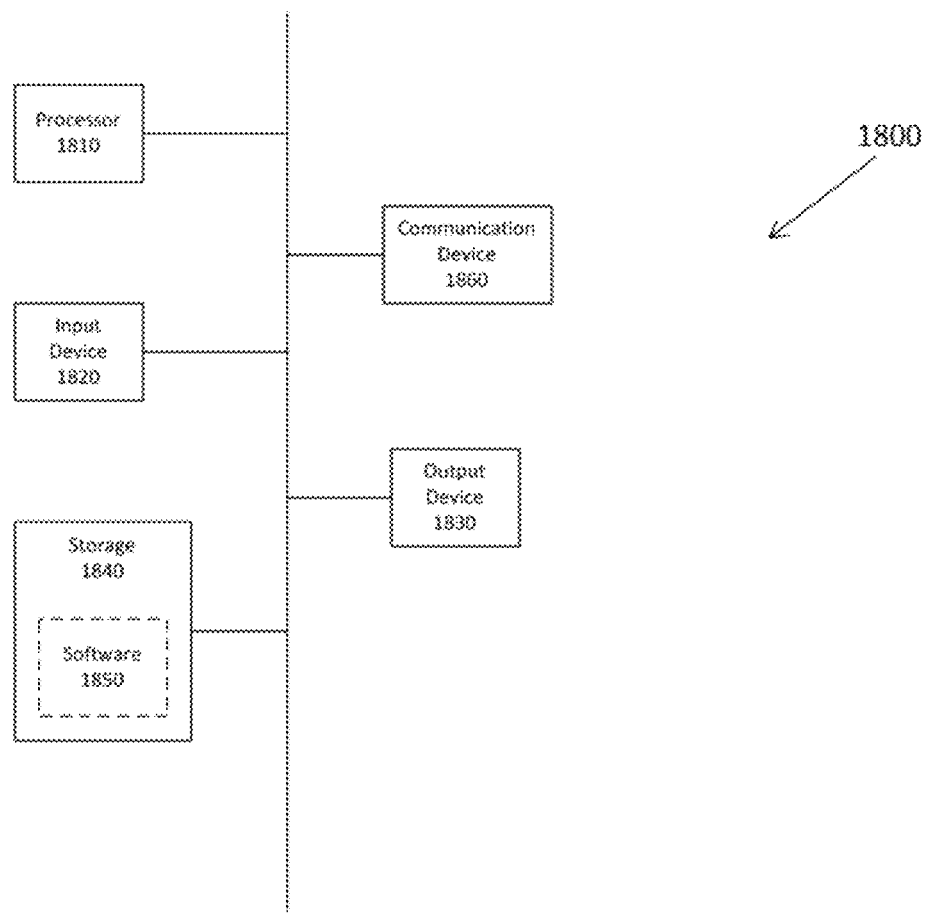
FIG. 18 illustrates an example of a computing system for generating a visualization, according to various embodiments.

FIG. 18 illustrates an example of a computing system, in accordance with some embodiments, for generating visualization according to the principles described herein. System 1800 can be used for one or more of subsystems 1702, 1704, and 1706 of system 1700. System 1800 can be a computer connected to a network, such as network 1708 of system 1700. System 1800 can be a client computer or a server. As shown in FIG. 18, system 1800 can be any suitable type of microprocessor-based system, such as a personal computer, workstation, server, or handheld computing device (portable electronic device) such as a phone or tablet. The system can include, for example, one or more of processor 1810, input device 1820, output device 1830, storage 1840, and communication device 1860. Input device 1820 and output device 1830 can generally correspond to those described above and can either be connectable or integrated with the computer.

Input device 1820 can be any suitable device that provides input, such as a touch screen, keyboard or keypad, mouse, or voice-recognition device. Output device 1830 can be any suitable device that provides output, such as a touch screen, haptics device, or speaker.

Storage 1840 can be any suitable device that provides storage, such as an electrical, magnetic, or optical memory including a RAM, cache, hard drive, or removable storage disk. Communication device 1860 can include any suitable device capable of transmitting and receiving signals over a network, such as a network interface chip or device. The components of the computer can be connected in any suitable manner, such as via a physical bus or wirelessly.

Software 1850, which can be stored in storage 1840 and executed by processor 1810, can include, for example, the programming that embodies the functionality of the present disclosure (e.g., as embodied in the devices as described above).

Software 1850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1840, that can contain or store programming for use by or in connection with an instruction execution system, apparatus, or device.

Software 1850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

System 1800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 1800 can implement any operating system suitable for operating on the network. Software 1850 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for displaying graphical indications associated with a joint, the method comprising, at a computing system:
   receiving image data associated with a joint of a subject;
   generating a three-dimensional model of at least a portion of the joint of the subject using the image data;
   identifying at least one region of the joint that deviates from a baseline anatomy by comparing at least a portion of the three-dimensional model to a baseline model;
   generating at least one measurement of a characteristic of the joint at one or more predefined locations using the three-dimensional model and a coordinate system;
   determining a pathology associated with the joint based on the at least one measurement of the characteristic of the joint; and
   generating and displaying a visualization for providing guidance for the surgical procedure on the at least one region of the joint, wherein the visualization comprises:
      a rendering of at least a portion of the three-dimensional model,
      a spectrum bar graph that comprises at least one representation of the at least one measurement of the characteristic of the joint, and
      at least one graphical indication indicating the pathology associated with the joint.

2. The method of claim 1, wherein the joint is a hip joint and the at least one measurement of the characteristic of the joint comprises at least one of an alpha angle measurement and a center edge angle measurement.

3. The method of claim 1, wherein the visualization comprises multiple spectrum bar graphs, each comprising a measurement of a different characteristic of the joint.

4. The method of claim 1, wherein the spectrum bar graph comprises regions that visually indicate normal, abnormal, and marginal anatomical measurement ranges associated with the at least one measurement of the characteristic of the joint.

5. The method of claim 1, wherein determining a pathology associated with the joint based on the at least one measurement of the characteristic of the joint comprises determining a potential instability based on an abnormal measurement of the characteristic of the joint.

6. The method of claim 5, wherein the at least one graphical indication indicates the potential instability.

7. The method of claim 1, wherein the joint is a hip joint and the deviation from the baseline anatomy is associated with at least one of a cam-type impingement and a pincer-type impingement.

8. The method of claim 1, wherein the spectrum bar graph comprises multiple representations of multiple measurements of the characteristic of the joint, each measurement associated with a different predefined location of the joint.

9. The method of claim 1, comprising receiving a user input associated with the displayed rendering and modifying the displayed rendering based on the user input.

10. The method of claim 1, wherein the image data comprises at least one of an MRI scan and CT scan.

11. The method of claim 1, wherein the baseline model is a model derived from a reference patient population.

12. A system for displaying graphical indications associated with a joint, the system comprising one or more processors, memory, and one or more programs, wherein the one or more programs are stored in the memory and configured to be executed by the one or more processors, the one or more programs including instructions for:
receiving image data associated with a joint of a subject;
generating a three-dimensional model of at least a portion of the joint of the subject using the image data;
identifying at least one region of the joint that deviates from a baseline anatomy by comparing at least a portion of the three-dimensional model to a baseline model;
generating at least one measurement of a characteristic of the joint at one or more predefined locations using the three-dimensional model and a coordinate system;
determining a pathology associated with the joint based on the at least one measurement of the characteristic of the joint; and
generating and displaying a visualization for providing guidance for the surgical procedure on the at least one region of the joint, wherein the visualization comprises:
a rendering of at least a portion of the three-dimensional model,
a spectrum bar graph that comprises at least one representation of the at least one measurement of the characteristic of the joint, and
at least one graphical indication indicating the pathology associated with the joint.

13. The system of claim 12, wherein the joint is a hip joint and the at least one measurement of the characteristic of the joint comprises at least one of an alpha angle measurement and a center edge angle measurement.

14. The system of claim 12, wherein the visualization comprises multiple spectrum bar graphs, each comprising a measurement of a different characteristic of the joint.

15. The system of claim 12, wherein the spectrum bar graph comprises regions that visually indicate normal, abnormal, and marginal anatomical measurement ranges associated with the at least one measurement of the characteristic of the joint.

16. The system of claim 12, wherein determining a pathology associated with the joint based on the at least one measurement of the characteristic of the joint comprises determining a potential instability based on an abnormal measurement of the characteristic of the joint.

17. The system of claim 16, wherein the at least one graphical indication indicates the potential instability.

18. The system of claim 12, wherein the joint is a hip joint and the deviation from the baseline anatomy is associated with at least one of a cam-type impingement and a pincer-type impingement.

19. The system of claim 12, wherein the spectrum bar graph comprises multiple representations of multiple measurements of the characteristic of the joint, each measurement associated with a different predefined location of the joint.

20. The system of claim 12, wherein the one or more programs include instructions for receiving a user input associated with the displayed rendering and modifying the displayed rendering based on the user input.

21. The system of claim 12, wherein the image data comprises at least one of an MRI scan and CT scan.

* * * * *